United States Patent
Ricci et al.

(10) Patent No.: US 12,008,749 B2
(45) Date of Patent: Jun. 11, 2024

(54) DENTAL IMAGES CORRELATED TO THE HUMAN GENOME WITH ARTIFICIAL INTELLIGENCE

(71) Applicants: Richard Ricci, New York, NY (US); Andrea Cambria, New York, NY (US)

(72) Inventors: Richard Ricci, New York, NY (US); Andrea Cambria, New York, NY (US)

(*) Notice: Subject to any disclaimer, the term of this patent is extended or adjusted under 35 U.S.C. 154(b) by 100 days.

(21) Appl. No.: 17/162,985

(22) Filed: Jan. 29, 2021

(65) Prior Publication Data
US 2021/0350530 A1    Nov. 11, 2021

Related U.S. Application Data

(63) Continuation-in-part of application No. 16/870,749, filed on May 8, 2020, now Pat. No. 10,937,160.

(51) Int. Cl.
| | | |
|---|---|---|
| G06T 7/00 | (2017.01) | |
| G06T 7/20 | (2017.01) | |
| G06T 7/41 | (2017.01) | |
| G16H 10/60 | (2018.01) | |
| G16H 30/20 | (2018.01) | |
| G16H 30/40 | (2018.01) | |

(52) U.S. Cl.
CPC .......... *G06T 7/0012* (2013.01); *G06T 7/20* (2013.01); *G06T 7/41* (2017.01); *G16H 10/60* (2018.01); *G16H 30/20* (2018.01); *G16H 30/40* (2018.01); *G06T 2207/10116* (2013.01); *G06T 2207/20036* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 10,937,160 B1* | 3/2021 | Ricci | G16H 80/00 |
| 10,991,094 B2* | 4/2021 | Kim | G16H 50/20 |
| 2013/0231960 A1* | 9/2013 | Lorsch | G16B 50/00 705/3 |
| 2014/0118355 A1* | 5/2014 | Vassilvitskii | G06F 16/9024 345/440 |

(Continued)

OTHER PUBLICATIONS

Gevaert, Olivier, et al. "Non-small cell lung cancer: identifying prognostic imaging biomarkers by leveraging public gene expression microarray data—methods and preliminary results." Radiology 264.2 (2012): 387-396. (Year: 2012).*

*Primary Examiner* — Michelle M Entezari Hausmann

(57) ABSTRACT

The field of the invention relates to a system to provide artificial intelligence processing of a dental image for determining a relative health risk, i.e. the probability of getting a human disease based on dental x-ray pathologies. The dental image or image (received from a source such as an x-ray, a camera, or an image capturing device) may be matched to a known computer stored genomic pathology dataset, such as a DNA dataset or a RNA dataset. Anatomic variances on a dental x-ray, such as periodontitis (bone disease associated with teeth), can be matched and identified to a known genomic pathology dataset, such as a diabetes DNA dataset, by an artificial intelligence system to produce at least one of: a relative pathology health risk, a treatment recommendation, a product recommendation for an individual patient.

20 Claims, 15 Drawing Sheets

(56) References Cited

U.S. PATENT DOCUMENTS

| | | | | |
|---|---|---|---|---|
| 2015/0086104 | A1* | 3/2015 | Miyamoto | C12Q 1/68 |
| | | | | 382/133 |
| 2015/0112702 | A1* | 4/2015 | Joao | G16H 10/60 |
| | | | | 705/2 |
| 2017/0329866 | A1* | 11/2017 | Macpherson | G16B 10/00 |
| 2019/0005684 | A1* | 1/2019 | De Fauw | G06T 11/003 |
| 2019/0326022 | A1* | 10/2019 | El-kalliny | G16H 80/00 |
| 2020/0410649 | A1* | 12/2020 | Kearney | A61B 5/7267 |
| 2021/0230701 | A1* | 7/2021 | Kitchen | C12Q 1/6886 |
| 2021/0342947 | A1* | 11/2021 | Takabayashi | G16H 30/20 |
| 2022/0148178 | A1* | 5/2022 | Glas | G16H 10/40 |
| 2022/0165391 | A1* | 5/2022 | Cameron | G16H 20/70 |
| 2022/0315984 | A1* | 10/2022 | Edelman | C12N 15/1065 |

* cited by examiner

DENTAL IMAGES CORRELATED TO THE HUMAN GENOME WITH ARTIFICIAL INTELLIGENCE

CLAIM OF PRIORITY

This application claims priority to U.S. Application 62/955,321 filed Dec. 30, 2019, the contents of which are herein fully incorporated by reference in its entirety.

FIELD OF THE INVENTION

The field of the invention relates to a system to provide artificial intelligence processing of a dental image for determining a relative health risk, i.e. the probability of getting a human disease based on a dental x-ray pathology. The dental image or image (received from a source such as an x-ray, a camera, or an image capturing device) may be matched to a known computer stored genomic pathology dataset, such as a DNA dataset or a RNA dataset. Anatomic variances on a dental x-ray, such as periodontitis (bone disease associated with teeth), can be matched and identified to a known genomic pathology dataset, such as a diabetes DNA dataset, by an artificial intelligence system to produce at least one of: a relative pathology health risk, a treatment recommendation, a product recommendation for an individual patient.

BACKGROUND OF THE INVENTION

Existing techniques for generating a dental recommendation based on dental image processing are deficient with regard to several aspects. For instance, current technologies do not generate a dental treatment recommendation (such as a root canal) or a dental product recommendation (such as an orthodontic aligner) based on an artificial intelligence model's processing of a dental image or a dental image landmark. Further, current technologies do not address e-commerce transactions of dental treatment recommendations or dental product recommendations between at least one of: a dental professional, a health care professional, an expert, an individual, an e-commerce organization, an artificial intelligence system, a researcher, a manufacturer, a business, an application software, a patient portal, a system software, a client device, a processing device.

Artificial intelligence systems have become routinely incorporated into our daily lives. The use of voice recognition digital assistants is a common interactive activity for many cell phone users. Digital assistant, suggest digital content based on a users prior content history. Facial recognition systems may utilize a combination of structured light and infrared red light with an artificial intelligence algorithm to produce a 3D textured model of a user's face. Users may unlock their cell phones and process financial transactions utilizing facial recognition. Further, facial recognition systems that utilize artificial intelligence and recurrent neural networks can identify and classify a facial image with the same accuracy as a human.

Big data deals with datasets that are too large for traditional data processing. Big data is collectively created from merging a huge volume of data compiled from the internet and is frequently used for predictive business decisions. Big data requires many redundant and complicated mathematical tasks to be delegated to artificial intelligence models. These models can be allowed to run unsupervised and unbiased. Human rules and training may be provided to artificial intelligence models. Artificial intelligence models may use electronic sensors (e.g., computer vision, pressure sensors, smoke detectors and microphones) and human training to teach computers to process the five senses with big data analytics. Techniques such as non-linear regression, exponential powers laws, geometric series, binomial distribution may also be used in analyzing big data analytics. Currently, there is a need for training artificial intelligent models with big data and sensors to generate dental treatment recommendations and dental product recommendations.

Digital medical images have led to vast improvements in patient diagnosis and treatment planning options. Constantly evolving medical image technologies have allowed many redundant and complicated mathematical tasks to be delegated to artificial intelligence models with reactive and limited memory capacities to process big data. Advances in computer science artificial intelligence models have revolutionized medical image diagnostic methods and enable users to manage digital images with extreme speed and accuracy. Unfortunately, dental image diagnosis models and dental image artificial intelligence diagnostic models have not been developed yet and there is a need for the development of these technologies.

SUMMARY OF THE EMBODIMENT

Dental images processed with artificial intelligence for e-commerce is described. In an example scenario, a processing device receives at least one of: a dental image, a dental image landmark, an image, an image landmark. A dental image or a dental image landmark may be matched and identified with a supervised annotated dental anatomy landmark dataset, an unsupervised annotated dental anatomy landmark dataset, a supervised annotated dental pathology landmark dataset, an unsupervised annotated dental pathology landmark dataset with a deep neural network by at least one of: a machine learning system, a deep learning system. At least one deep neural network may learn to detect different dental image landmarks of a dental image and match and identify to a supervised annotated dental anatomy landmark dataset, an unsupervised annotated dental anatomy landmark dataset, a supervised annotated dental pathology landmark dataset, an unsupervised annotated dental pathology landmark dataset to produce a real time confidence score of at least one of: a dental anatomy landmark, a dental pathology landmark and provide to a real time dental image dataset.

At least one of: a supervised annotated dental anatomy landmark dataset, an unsupervised annotated dental anatomy landmark dataset, a supervised annotated dental pathology landmark dataset, an unsupervised annotated dental pathology landmark dataset may be at least one of: obtained, annotated from at least one of: a dental professional, a health care professional, an expert, an individual, an e-commerce organization, an artificial intelligence system, a researcher, a manufacturer, a business, an application software, a patient portal, a system software, a client device, an aggregator server, an aggregator service, a processing device. The aggregator service may be a data warehouse. An aggregator may also be a data house. The process may continue to match and identify a real time dental image dataset to at least one of: a supervised annotated dental treatment recommendation dataset, an unsupervised annotated dental treatment recommendation dataset to produce a real time confidence score for a dental treatment recommendation and provide this confidence score to a real time dental treatment recommendation dataset. An aggregate server and/or processing device may match and identify a real time dental image dataset and/or a real time dental treatment recommendation dataset to at least one of: a supervised annotated dental product recommendation dataset, an unsupervised annotated dental product recommendation dataset to produce one or more real time confidence scores of a dental product recommendation. These one or more real time confidence scores of a dental product recommendation may be provided to a real time dental product recommendation dataset. An example of a real time dental product recommendation may include recommending a specific orthodontic aligner or a manufacturer for an orthodontic aligner fabrication. Another example of a real time dental product recommendation may include a specific dental implant or a specific dental implant size based on a dental image.

The supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a biometric dataset and a real time correlation dataset are configured to continually merge and correlate additional annotated information from at least one of: a dental professional, a health care professional, an expert, an individual, an e-commerce organization, an artificial intelligence system, a researcher, a manufacturer, a business, an application software, a patient portal, a system software, a client device, a processing device. Further, additional annotated dental images or dental image landmarks may be processed with supervised learning, unsupervised learning, rewards training, transfer learning, confidence values, confidence scores, reactive memory, non reactive memory, a memory of dataset, a system of artificial intelligence with memory. The supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a biometric dataset, a real time correlation dataset may be configured to identify and correct for missing information.

An artificial intelligence system may work individually or as a team in any order or combination. An artificial intelligence system does not necessarily imply sentient intelligence but may act as an interface of human interpretation rules and training that are provided to a single artificial intelligence system or a team of artificial intelligence systems. Further, an artificial intelligence system may be based on human interpretation rules and training.

At least one of: a dental professional, a health care professional, an individual, an expert, an individual, an e-commerce organization, an artificial intelligence system, a researcher, a manufacturer, a business, an application software, a patient portal, a system software, a machine learning mechanism, a deep learning mechanism may process a transaction of at least one of: an exchange, a transfer, a purchase, a sell of at least one of: a dental image, a dental image landmark, an image, an image landmark, a supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a biometric dataset, a real time correlation dataset over a communication network such as the internet, wherein a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform. Further, a processor configured for a dental professional or an individual to process a transaction of at least one of: an exchange, a transfer, a buy, a sell of at least one of: a dental image, a dental image landmark, an image, an image landmark, a supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a biometric dataset, a correlation dataset in exchange for at least one of: a currency, a data, a discount, a product, a good, a software, an application, an advertisement.

Further, a method of generating a dental recommendation based on image processing in accordance with some embodiments. The method may include receiving, using a processing device or a communication device, at least one patient data comprising at least one image from at least one patient device. The method may include retrieving, using a storage device, at least one dental dataset. The method may include analyzing, using a processing device, at least one patient data and at least one dental dataset. At least one dental dataset is associated with at least one patient data. The at least one dental dataset comprises at least one of a classified dental image anatomy dataset and a classified dental image pathology dataset. The method may include generating, using an processing device, at least one landmark based on an analyzing. At least one landmark comprises at least one dental characteristic associated with at least one patient data. The method may include retrieving, using a storage device, at least one dental reference dataset. The method may include processing, using a device, at least one landmark and at least one dental reference dataset. The method may include determining, using a processing device, at least one dental recommendation based on a processing. The method may include transmitting, using a processing device or a communication device, at least one dental recommendation to at least one external device. The method may include storing, using a storage device, at least one dental recommendation.

According to some embodiments, a system of generating a dental recommendation based on image processing is disclosed. The system may include a processing device or a communication device configured for receiving at least one patient data comprising at least one image from at least one patient device. The processing device or a communication device may be configured for transmitting at least one dental recommendation to at least one external device. The system may include a processing device configured for analyzing at least one patient data and at least one dental dataset. At least one dental dataset is associated with at least one patient data. At least one dental dataset comprises at least one of a classified dental image anatomy dataset and a classified dental image pathology dataset. The processing device may be configured for generating at least one landmark based on an analyzing. At least one landmark comprises at least one dental characteristic associated with at least one patient data. A processing device may be configured for processing at least one landmark and at least one dental reference dataset. A processing device may be configured for determining at least one dental recommendation based on a processing. The system may include a storage device configured for retrieving at least one dental dataset, retrieving at least one dental reference dataset and storing at least one dental recommendation.

Both the foregoing summary and the following detailed description provide examples and are explanatory only. Accordingly, the foregoing summary and the following detailed description should not be considered to be restrictive. Features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure.

The drawings may contain text or captions that may explain certain embodiments of the present disclosure. This text is included for illustrative, non-limiting, explanatory purposes of certain embodiments detailed in the present disclosure.

DETAILED DESCRIPTION OF THE INVENTION

Figure 1:
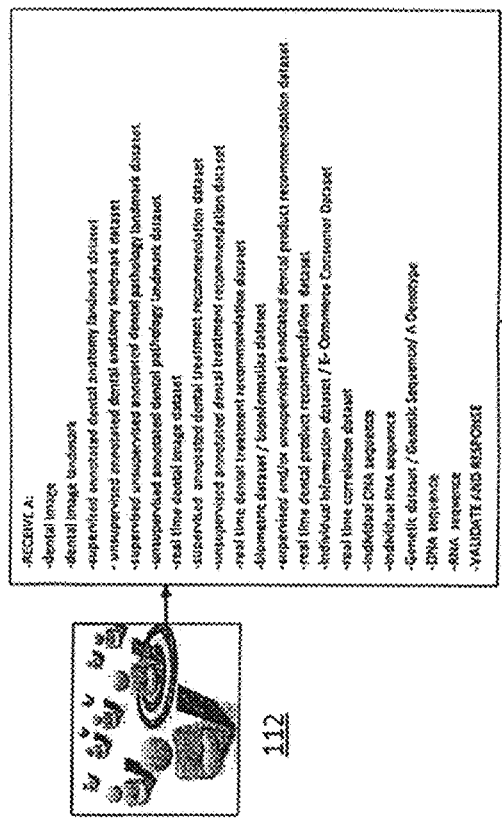
FIG. 1 is an illustration of an online platform consistent with various embodiments of the present disclosure.
Figure 1:
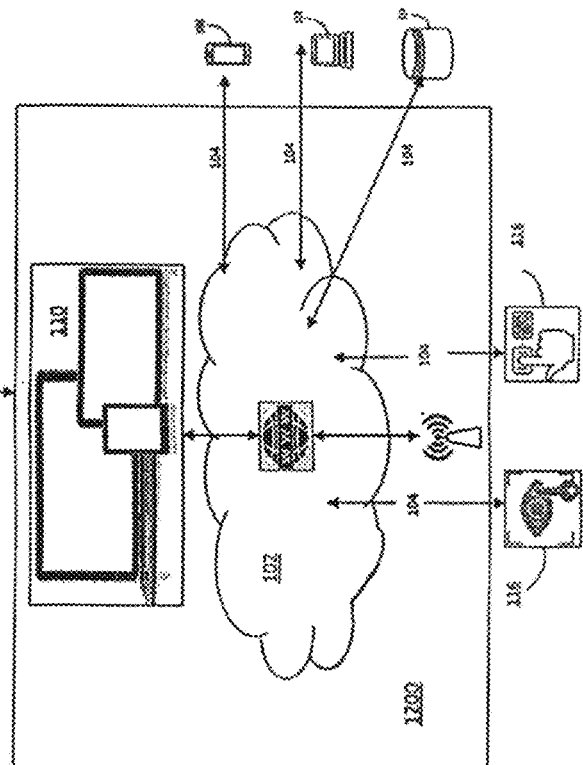

The field of the present invention relates to a system for providing artificial intelligence processing of at least one of: a dental image, a dental image landmark, an image, an image landmark for e-commerce. The dental image or dental image landmark, which may be obtained by image capture device, may be processed by at least one of: an artificial intelligence system, an artificial intelligence dataset, an artificial intelligence model to produce at least one of: a real time dental treatment recommendation, a real time dental treatment recommendation for no treatment, a real time dental product recommendation, a real time dental product recommendation for no product for e-commerce. As a preliminary matter, it will readily be understood by one having ordinary skill in the relevant art that the present disclosure has broad utility and application. As should be understood, any embodiment may incorporate only one or a plurality of the above-disclosed aspects of the disclosure and may incorporate only one or a plurality of the above-disclosed features. Any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope may be defined by the claims and the equivalents thereof.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order and may be omitted in any sequence or order. Indeed, the steps in such processes or methods generally may be carried out in various different sequences and orders while still falling within the scope of the present disclosure.

Additionally, it is important to note that each term used herein refers to that which an ordinary artisan would understand such term to mean based on the contextual use of such term herein. To the extent that the meaning of a term used herein, as understood by the ordinary artisan based on the contextual use of such term, differs in any way from any particular dictionary definition of such term, it is intended that the meaning of the term as understood by the ordinary artisan should prevail.

It is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods and systems of generating a dental recommendation based on image processing, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the internet. In some other embodiments, the method may be performed by one or more of at least one of: one server computer, one client device, one network device, one sensor. Examples of one or more client devices and/or a server computer may include, a desktop computer, a laptop computer, a tablet, a personal digital assistant, a portable electronic device, a wearable computer, a smartphone, an Internet of Things (IoT) device, a smart electrical appliance, a video game console, a rack server, a super-computer, a mainframe computer, a mini-computer, a micro-computer, a storage server, an application server, (a mail server, a web server, a real-time communication server, an FTP server, a virtual server, a proxy server, a DNS serve). One or more client devices and/or a server computer may be configured for executing a software application such as, for example, but not limited to, an operating system (e.g., Windows, macOS, Unix, Linux, Android) in order to provide a user interface (e.g., GUI, touch-screen based interface, voice-based interface, gesture-based interface) for use by one or more users and/or a network interface for communicating with other devices over a communication network. Accordingly, a processing device may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. A processing device may include a communication device configured for communicating with one or more external devices. One or more external devices may include, for example, but are not limited to, a client device, a third-party database, a public database, a private database. The processing device and/or a communication device may be configured for communicating with one or more external devices over one or more communication channels. One or more communication channels may include a wireless communication channel and/or a wired communication channel. Accordingly, a processing device and/or a communication device may be configured for performing transmitting and/or receiving of information in electronic form. A server computer may include a storage device configured for performing data storage and/or data retrieval operations. In general, a storage device may be configured for providing reliable storage of digital information. Accordingly, in some embodiments, a storage device may be based on technologies such as, but not limited to, data compression, data backup, data redundancy, deduplication, error correction, data finger-printing, role-based access control.

One or more steps of the method disclosed herein may be initiated, maintained, controlled and/or terminated based on a control input received from one or more devices operated by one or more users such as, for example, but not limited to, an end-user, an administrator, a service provider, a service consumer, an agent, a broker and a representative thereof. The user as defined herein may refer to a human, and/or an artificially intelligent system in any state of existence, unless stated otherwise, elsewhere in the present disclosure. In some embodiments, one or more users may be required to successfully perform authentication in order for the control input to be effective. In general, a user of the one or more users may perform authentication based on the possession of a secret human-readable secret data (e.g., username, password, passphrase, PIN, secret question, secret answer) and/or possession of a machine-readable secret data (e.g., encryption key, decryption key, bar codes) and/or possession of one or more embodied characteristics unique to the user (e.g., biometric variables such as but not limited to, fingerprint, palm-print, voice characteristics, behavioral characteristics, facial features, iris pattern, heart rate variability, evoked potentials, brain waves) and/or possession of a unique device (e.g., a device with a unique physical and/or chemical and/or biological characteristic, a hardware device with a unique serial number, a network device with a unique IP/MAC address, a telephone with a unique phone number, a smartcard with an authentication token stored thereupon). Accordingly, one or more steps of the method may include communicating via transmitting and/or receiving with one or more sensor devices and/or one or more actuators in order to perform authentication. For example, one or more steps may include receiving, using a processing device and/or a communication device, a secret human-readable data from an input device such as a keyboard, a keypad, a touch-screen, a microphone, a camera. Likewise, one or more steps may include receiving, using a processing device and/or a communication device, one or more embodied characteristics from one or more biometric sensors.

One or more steps of the method may be automatically initiated, maintained and/or terminated based on one or more predefined conditions. In an instance, one or more predefined conditions may be based on one or more contextual variables. In general, one or more contextual variables may represent a condition relevant to the performance of one or more steps of the method. One or more contextual variables may include, but are not limited to, location, time, identity of a user associated with a device (e.g., the server computer, a client device) corresponding to the performance of one or more steps, environmental variables (e.g., temperature, humidity, pressure, wind speed, lighting, sound) associated with a device corresponding to the performance of one or more steps, physical state and/or physiological state and/or psychological state of the user, physical state (e.g., motion, direction of motion, orientation, speed, velocity, acceleration, trajectory) of the device corresponding to the performance of one or more steps and/or semantic content of data associated with one or more users. Accordingly, one or more steps may include communicating with one or more sensors and/or one or more actuators associated with one or more contextual variables. For example, one or more sensors may include, but are not limited to, a timing device (e.g., a real-time clock), a location sensor (e.g., a GPS receiver, a GLONASS receiver, an indoor location sensor), a biometric sensor (e.g., a fingerprint sensor), an environmental variable sensor (e.g., temperature sensor, humidity sensor, pressure sensor) and a device state sensor (e.g., a power sensor, a voltage/current sensor, a switch-state sensor, a usage sensor-associated with the device corresponding to performance of one or more steps).

One or more steps of the method may be performed one or more number of times. Additionally, one or more steps may be performed in any order other than as exemplarily disclosed herein, unless explicitly stated otherwise elsewhere in the present disclosure. Two or more steps of the one or more steps may, in some embodiments, be simultaneously performed, at least in part. In some embodiments, there may be one or more time gaps between the performance of any two steps of the one or more steps. Further, at least one of: a processing device, a processing service, an aggregator, aggregator server, a communication device is configured to at least one of: execute an instruction in any order, omit an instruction in any order. Wherein an instruction may include one of: a match, an identify, a score, a rule, a train, a process, an exchange, a transfer, a purchase, a sell, a receive, a retrieve, a transmit, an analyze, a generate, a transmit, an order.

In some embodiments, one or more predefined conditions may be specified by one or more users. Accordingly, one or more steps may include receiving, using a processing device and/or a communication device, one or more predefined conditions from one or more and devices operated by one or more users. One or more predefined conditions may be stored in a storage device. Alternatively, and/or additionally, in some embodiments, one or more predefined conditions may be automatically determined, using a processing device, based on historical data corresponding to performance of one or more steps. For example, the historical data may be collected, using a storage device, from a plurality of instances of performance of the method. Such historical data may include performance actions (e.g., initiating, maintaining, interrupting, terminating) of one or more steps and/or one or more contextual variables associated therewith. Machine learning and/or deep learning may be performed on the historical data in order to determine one or more predefined conditions. For instance, machine learning of historical data may determine a correlation between one or more contextual variables and performance of one or more steps of the method. Accordingly, the one or more predefined conditions may be generated, using a processing device, based on a correlation.

One or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data there between corresponding to one or more steps of the method. For example, in a client-server environment, sensitive data corresponding to a user may not be allowed to be transmitted to a server computer. Accordingly, one or more steps of the method operating on a sensitive data and/or a derivative data thereof may be performed on the client device.

FIG. 1 is an illustration of an online platform 100 consistent with various embodiments of the present disclosure.

By way of non-limiting example, the online platform 100 to facilitate generation of a dental recommendation based on image processing may be hosted on a centralized server 102, such as, for example, a cloud computing service. The centralized server 102 may communicate with other network entities, such as, for example, a mobile device 106 (such as a smartphone, a laptop, a tablet computer), electronic devices 110 (such as desktop computers, server computers), databases 114, sensors 116, over a communication network 104, such as, but not limited to, the internet. Users of the online platform 100 may include relevant parties such as, but not limited to, end users, and administrators. Accordingly, in some instances, electronic devices operated by the one or more relevant parties may be in communication with the online platform 100. A user 112, such as one or more relevant parties, may access online platform 100 through a web based software application or browser. A web based software application may be embodied as, for example, but not be limited to, a website, a web application, a desktop application, and a mobile application compatible with a computing device 1200.

Figure 2:
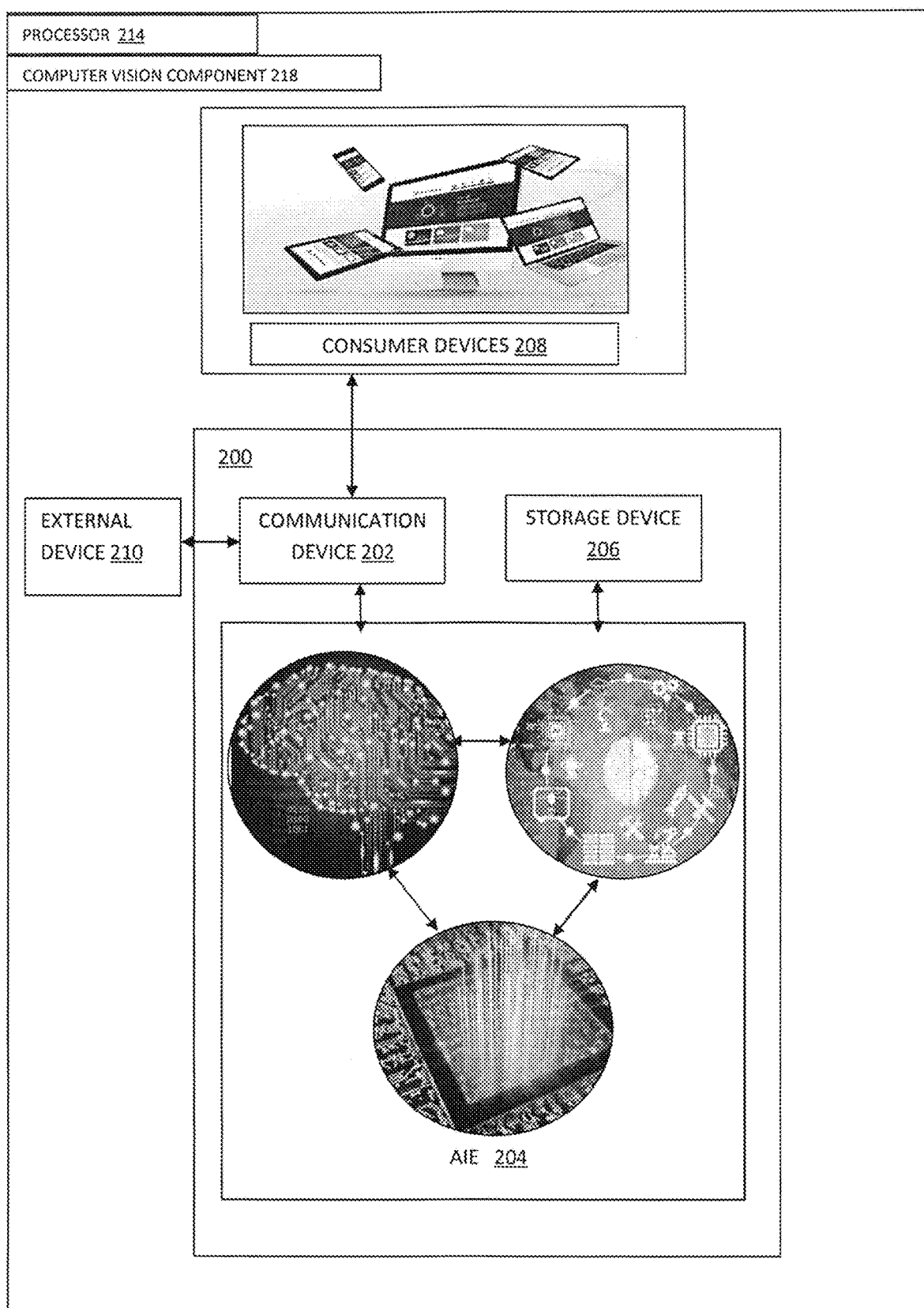
FIG. 2 is an illustration diagram of a system for facilitating generating a dental recommendation based on image processing, in accordance with some embodiments.

FIG. 2 is an illustration diagram of a system 200 for generating a dental recommendation based on image processing, in accordance with some embodiments. Accordingly, system 200 may include a communication device 202, a processing device 204 and a storage device 206. A communication device 202 may be configured for receiving at least one patient data comprising at least one image from at least one patient device 208. A communication device 202 may be configured for transmitting at least one dental recommendation to at least one external device 210. At least one patient data may include an individual information dataset and/or a personal information associated with at least one patient. At least one of: one patient data, an individual information dataset, a personal information may include at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a change of location, a biometric measurement, a biometric sensor measurement, a genetic dataset, an internet browsing history, a dataset. At least one patient device 208 may include at least one user device and at least one diagnosis device, wherein at least one user device is associated with at least one patient, wherein at least one diagnosis device is configured for generating a diagnosing data. At least one user device may include a smartphone, a tablet, a mobile, a personal computer, a laptop. At least one diagnosing device may include an x-ray, a camera, a toothbrush with imaging device, toothbrush with imaging device a being camera, an intraoral scanner, a magnetic resonance image (MRI) device, a computed tomography (CT) scan equipment, cone beam computed tomography (CBCT) device, a scintillator technology based imaging machine, a trans-illumination imaging machine, a fluorescence technology based imaging machine, a blue fluorescence technology based imaging machine, a laser based technology based imaging machine, an indirect or direct flat panel detector (FPD), a charged couple device (CCD), a phosphor plate radiography device, a picture archiving and communication system (PACS), a photo-stimulable phosphor (PSP) device, a wireless complementary metal-oxide-semiconductor (CMOS) device. In some embodiments, at least one external device 210 may be associated with the at least one patient device 208. At least one external device 210 may include a smartphone, a tablet, a mobile, a personal computer, a laptop. In some embodiments, the at least one external device 210 may be associated with a second user. A second user may include a dental professional, a health care professional, an expert, an individual, an e-commerce organization, an artificial intelligence system, a researcher, a manufacturer, a business, an application software, a patient portal, a system software, a client device, a processing device. A processing device 204 may be configured for analyzing at least one patient data and at least one dental dataset. At least one dental dataset may be associated with the at least one patient data. At least one dental dataset may include at least one of a classified dental image anatomy dataset and a classified dental image pathology dataset.

In some embodiments, the analyzing of at least one patient data and at least one dental dataset may be based on at least one first artificial intelligence model. At least one first artificial intelligence model may be configured for identifying of at least one dental characteristic associated with at least one patient data. At least one first intelligence model comprises at least one of a deep neural network model, a machine learning model, a recurrent neural network model, a deep forest decision tree, and an independent neural network model. At least one first artificial intelligence model may include a computer vision model.

In an embodiment, at least one first artificial intelligence model may be trained based on a confidence score associated with at least one image. A confidence score may be provided by at least one expert. At least one first artificial intelligence model may be trained for identifying of at least one dental characteristic. A processing device 204 may be configured for generating at least one landmark based on analyzing. At least one landmark comprises at least one dental characteristic associated with the at least one patient data. The processing device 204 may be configured for processing at least one landmark and at least one dental reference dataset. Additionally, a processing device 204 may be configured for determining at least one dental recommendation based on a processing.

In some embodiments, processing of at least one landmark and at least one dental reference may be based on at least one second artificial intelligence model. At least one second artificial intelligence model may be configured for determining of at least one dental recommendation. At least one second intelligence model comprises at least one of a deep neural network model, a machine learning model, a recurrent neural network model, a deep forest decision tree, and an independent neural network model. At least one second artificial intelligence model may include a computer vision model. In an embodiment, at least one second artificial intelligence model may be trained based on a confidence score associated with at least one image. The confidence score may be provided by at least one expert. At least one second artificial intelligence model may be trained for determining of at least one dental recommendation. A storage device 206 may be configured for retrieving at least one dental dataset, retrieving at least one dental reference dataset and storing at least one dental recommendation.

In an embodiment, at least one second artificial intelligence model may be trained based on at least one of: a dental image dataset, a dental image treatment dataset, a dental product dataset, a dental image landmark dataset and the an artificial intelligence dataset. Additionally, at least one first artificial intelligence model may be trained based on at least one of: a dental image dataset, a dental image-treatment dataset, a dental product dataset, a dental image landmark dataset, an artificial intelligence dataset. In an embodiment, a communication device 202 is configured for transmitting a dental professional referral to the at least one external device 210. A processing device 204 is configured for analyzing at least one of: a provider dataset, at least one image, a dental treatment data, a dental image treatment dataset, a dental product dataset, a dental image landmark dataset, and the artificial intelligence dataset to generate a dental professional referral, wherein a provider dataset may include a dental professional, a dental specialist, a health care professional, a health care specialist, a dentist, a dental specialist, a hygienist, a dental assistant, a dental staff member, a dental laboratory technician, a physician, a physician specialist, a nurse, a medical technician, an veterinarian, a veterinarian professional.

According to some embodiments, at least one external device 210 may include at least one first user device associated with at least one first user. At least one first user may include a dental professional, a health care professional, an expert, an individual, an e-commerce organization, an artificial intelligence system, a researcher, a manufacturer, a business, an application software, a patient portal, a system software, a client device, a processing device. A dental professional may include a dentist, a hygienist, a dental assistant, a dental staff member, a medical staff member, a dental laboratory technician, a physician, a nurse, a medical technician, a veterinarian, a veterinarian professional, a licensed professional. An e-commerce organization may include a business, a business entity, a business owner, an employer, a wholesaler, a retailer, a group, a research entity, a law enforcement entity, a public administration entity, a government agency, an administrator, an administrator entity, a governing agency, a bioinformatics service, an insurance company, a cloud based storage service. At least one first user device may include a smart phone, a tablet, a laptop, a personal computer. A communication device 202 may be configured for transmitting a request to at least one first user device of at least one external device 210, receiving at least one first user data from at least one first user device; and transmitting a notification to at least one patient device 208 and at least one external device 210. At least one first user data may include certifications, qualification proof, license number that may be verified. A processing device 204 may be configured for analyzing at least one first user data based on at least one regulatory data and generating the notification corresponding to at least one first user based on the analyzing of at least one first user data. A storage device 206 may be configured for retrieving at least one regulatory data based on at least one first user.

According to some embodiments, a communication device 202 is configured for receiving a transaction request from at least one external device 210, transmitting a transaction request to at least one first user device, receiving a transaction response from at least one first user device, and transmitting a transaction response to at least one external device 210. A transaction request may include a request for a transaction of at least one of: a one patient data, a dental image dataset, a dental image treatment dataset, a dental product dataset, at least one dental dataset, a dental image landmark dataset. A transaction may include at least one of: business to business (B2B), business to consumer (B2C), consumer to business (C2B), consumer to consumer (C2C), business to administration (B2A), and consumer to administration (C2A) in exchange for at least one of: a currency, a data, a discount, a product, a good, a software, an application, an advertisement.

In an embodiment, at least one of: one image, one landmark, one patient data, a dental image dataset, a dental image treatment dataset, a dental product dataset, at least one dental dataset, a dental image landmark dataset is configured to compensate for distorted and/or missing image information associated with at least one image. At least one dental recommendation may include at least one of: a real time dental treatment recommendation, a real time dental treatment recommendation for no treatment, a real time dental product recommendation, a real time dental product recommendation for no product.

A communication device 202 may be configured for transmitting at least one dental recommendation and at least one patient data to at least one of: an expert device, a processing device, a patient device associated with at least one expert. At least one expert may include a dental professional, a healthcare professional. A communication device 202 may be configured for receiving a first confidence score from at least one of: an expert device, a processing device, a patient device. A first confidence score may be associated with at least one dental recommendation. A communication device 202 may be configured for transmitting a first confidence score to at least one external device 210. A first confidence score may include a measure of appreciation. A first confidence score may include a rating, a score. At least one of: an expert device, a processing device, a patient device may include a smartphone, a tablet, a laptop, a personal computer, a server, a desktop computer, a workstation, a laptop computer, a cell phone, a tablet, a mobile device, a cloud based storage service. A real time dental product recommendation may include at least one of: no dental product, at least one dental product, an orthodontic aligner, a dental implant, a crown, a membrane, a graft, a screw, a composite, an amalgam, a dental material, a preventive material, an impression material, a dental instrument.

At least one dental recommendation may include a treatment option aid and/or a treatment demonstration aid. In an embodiment, a processing device 204 is configured for analyzing at least one dental recommendation to generate a visual representation corresponding to at least one dental recommendation. A visual representation may include at least one of: a number, a percentage, a percent, a proportion, a ratio, a graph, a color, an image, a score, a grade, a count, a rate, an average, a figure, an outline, an area, a shading. A storage device 206 is configured for storing the visual representation.

According to embodiments, the processing device 204 may be configured for updating at least one dental reference dataset with at least one patient data and at least one dental recommendation based on a first confidence score and generating at least one updated reference dataset based on updating of at least one dental reference dataset. The storage device 206 may be configured for storing at least one updated reference dataset. A communication device 202 may be configured for receiving an order from at least one patient device 208. An order may be associated with at least one dental recommendation, transmitting an order to at least one external device 210, receiving a response corresponding to an order from at least one external device 210 and transmitting a response to at least one patient device 208. Further, a communication device 202 may be configured for transmitting at least one patient data and at least one landmark to at least one of: an expert device, a processing device, a patient device, receiving at least one of: a second confidence score, a multiple confidence score from at least one of: an expert device, a processing device, a patient device. At least one of: a second confidence score, a multiple confidence score may be associated with at least one landmark and transmitting at least one of: a second confidence, a multiple confidence score to at least one external device 210.

According to embodiments, a communication device 202 may be configured for transmitting a validity notification to at least one external device 210. A processing device 204 may be configured for analyzing at least one patient data and at least one dental dataset and generating a validity notification corresponding to at least one patient data based on analyzing. A validity notification may be associated with a measure of approval of at least one patient data.

In an embodiment, an e-commerce organization may include a dental insurance service, wherein the dental insurance service provides an insurance dataset including at least one of an American Dental Association (ADA) code, a date, a claim identifier, a claim number, a duplicate claim associated with the claim identifier, a provider national identification number, a provider's state license number, a provider identification number may be correlated to the insurance dataset. Wherein, the insurance dataset may be correlated to least one of: a dental image 1002, a dental image 1016 landmark, an individual information dataset and provided to a real time correlation dataset. A processing device 204 is configured for merging the insurance dataset and the artificial intelligence dataset to generate a first updated artificial intelligence dataset. A communication device 202 is configured for transmitting a first updated artificial intelligence dataset to at least one external device 210. A dental insurance service may include an insurance company and/or a claims data warehouse. A dental insurance service may be an insurance company.

In an embodiment, the e-commerce organization includes a bioinformatics service, and wherein the bioinformatics service provides a bioinformatics dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, a diabetes diagnosis. Wherein, a bioinformatics dataset may also be correlated to least one of: a dental image 1002, a dental image landmark 1016, an individual information dataset and provided to a real time correlation dataset. A processing device 204 is configured for merging a bioinformatics dataset and an artificial intelligence dataset to generate a second updated artificial intelligence dataset. A communication device 202 is configured for transmitting a second updated artificial intelligence dataset to at least one external device 210. A bioinformatics service may be a genetic testing service, a genotyping service. A bioinformatics service may be provided by a bioinformatics organization (such as a personal genomic or research organization).

In an embodiment, an artificial intelligence dataset may include at least one patient compliance factor corresponding to at least one patient. A processing device 204 is configured for analyzing at least one patient compliance factor to determine at least one treatment obstacle, wherein the treatment obstacle may include a financial obstacle. A storage device 206 is configured for retrieving details of at least one third party financing company based on a treatment obstacle. A communication device 202 is configured for transmitting the details of at least one third party financing company to at least one external device 210. At least one patient compliance factor may include insurance maximum, remaining benefits, missed appointments, rescheduled appointments, dental phobia, financial challenges, lifestyle changes, business plans, travel plans, illness, injury.

In an embodiment, a communication device 202 is configured for receiving at least one post treatment data associated with at least one patient from at least one patient device 208. A processing device 204 is configured for analyzing at least one post treatment data and an artificial intelligence dataset based on at least one patient compliance factor to generate a treatment confidence score, wherein at least one patient compliance factor may include number of individual visits, number of broken appointments, failure to complete treatment rate, an ASA grade, a smoker, a diabetic, a biologic medication. A communication device 202 is configured for transmitting a treatment confidence score to at least one external device 210.

In an embodiment, a processing device 204 is configured for analyzing an artificial intelligence dataset to identify geographic dental visit movement associated with the at least one patient. A communication device 202 is configured for transmitting the dental visit movement to at least one external device 210. Geographic dental visit movements may facilitate tracking at least one of: a missing person, a person of interest, an abducted child. In an embodiment, a processing device 204 is configured for a system of rewards training and/or transfer learning. A processing device 204 may be coupled with an object tracking mechanism configured to track objects in at least one of at least one dental image 1002 and at least one landmark. In an embodiment, processing device 204 is configured for Natural Language Processing (NLP).

Figure 3:
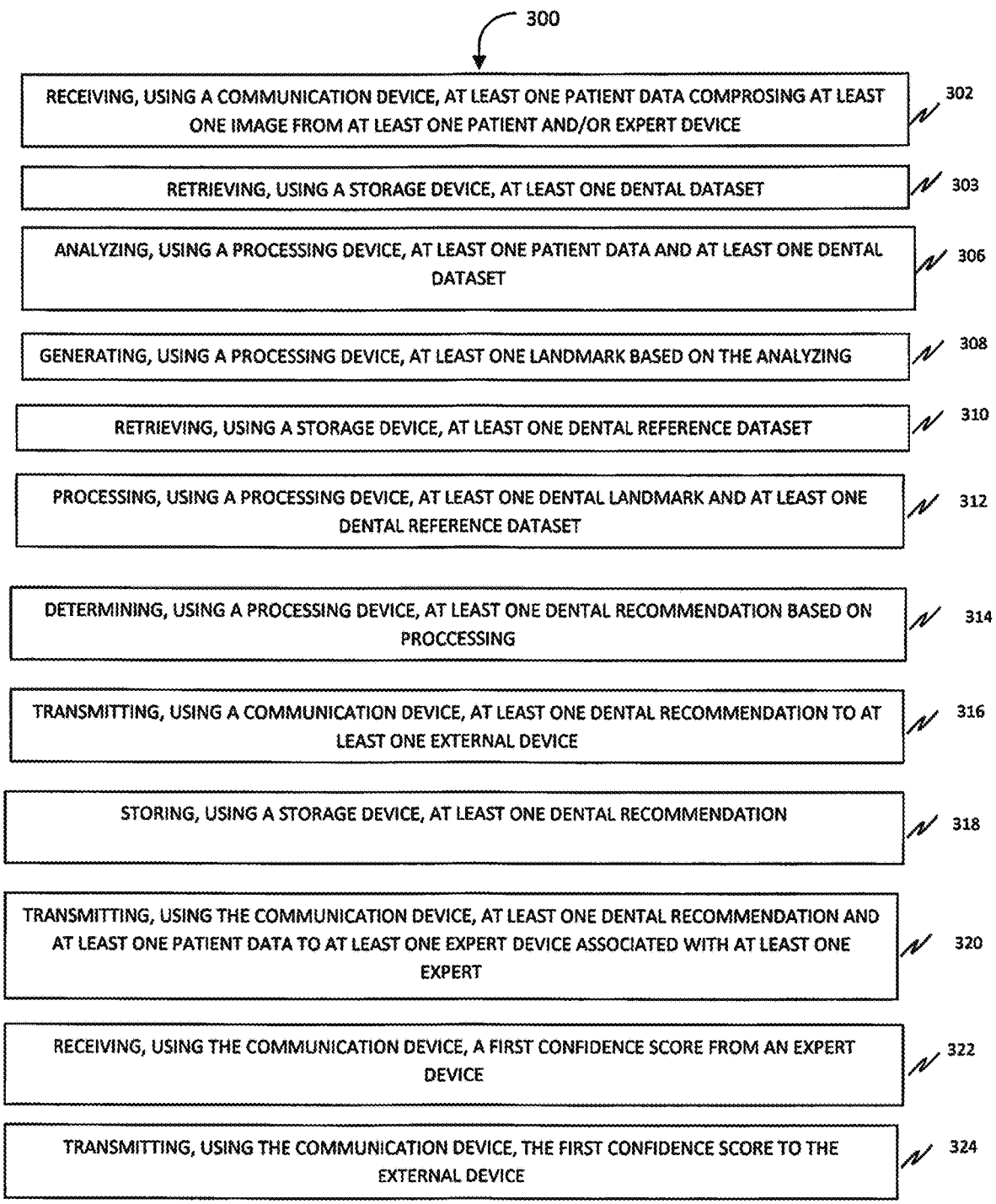
FIG. 3 is a flowchart of a method of generating a dental recommendation based on image processing, in accordance with some embodiments.

FIG. 3 is a flowchart of method 300 for generating a dental recommendation based on image processing, in accordance with some embodiments. At 302, method 300 may include receiving, using a processing device 214 and/or a communication device, at least one patient data comprising at least one image from at least one patient device. At least one patient data may include an individual information dataset and/or a personal information and a dental image 1002 associated with at least one patient. An individual information dataset and/or a personal information may include a name, an identification number, an address, a contact information, a medical history. At least one patient device may include at least one user device and at least one diagnosis device, wherein at least one user device is associated with at least one patient, wherein at least one diagnosis device is configured for generating a diagnosing data. At least one user device may include a smartphone, a tablet, a mobile, a personal computer, a laptop, a At least one diagnosing device may include an x-ray, a camera, an image capturing device, a toothbrush with imaging device, a toothbrush with imaging device a being camera, an intraoral scanner, a magnetic resonance image (MRI) device, a computed tomography (CT) scan equipment, cone beam computed tomography device.

At 304, method 300 may include retrieving, using a storage device, at least one dental dataset.

At 306, method 300 may include analyzing, using a processing device, at least one patient data and at least one dental dataset. At least one dental dataset is associated with at least one patient data. At least one dental dataset comprises at least one of a classified dental image anatomy dataset and a classified dental image pathology dataset.

According to an embodiments, an analyzing of at least one patient data and at least one dental dataset may be based on at least one first artificial intelligence model. At least one first artificial intelligence model may be configured for identifying at least one dental characteristic associated with at least one patient data. At least one first artificial intelligence model comprises at least one of: a deep neural network model, a machine learning model, a recurrent neural network model, a deep forest decision tree, an independent neural network model, an artificial intelligence platform. In an embodiment, at least one first artificial intelligence model may be trained based on a confidence score associated with at least one image. A confidence score may be provided by at least one expert.

At 308, method 300 may include generating, using a processing device, at least one landmark based on an analyzing. At least one landmark comprises at least one dental characteristic associated with at least one patient data. At 310, method 300 may include retrieving, using a storage device, at least one dental reference dataset. In some embodiments, at least one dental reference dataset comprises at least one of: a dental treatment dataset, a dental image treatment dataset, a dental product dataset, a dental image landmark dataset, wherein the processing device is configured for merging at least one of: a dental treatment data, a dental image treatment dataset, a dental product dataset, a dental image landmark dataset to generate an artificial intelligence dataset, wherein an analyzing of at least one patient data and at least one dental dataset may be based on an artificial intelligence dataset. At 312, method 300 may include processing, using processing device, at least one landmark and at least one dental reference dataset.

According to some embodiments, a processing of at least one landmark and at least one dental reference dataset may be based on at least one second artificial intelligence model and/or a team of artificial intelligence models, wherein at least one of: a second artificial intelligence model, a team of artificial intelligence models is configured for determining of at least one dental recommendation. At least one second artificial intelligence model may include at least one of: a deep neural network model, a machine learning model, a recurrent neural network model, a deep forest decision tree, an independent neural network model. In an embodiment, at least one second artificial intelligence model may be trained based on a confidence score associated with at least one image. A confidence score may be provided by at least one expert.

At 314, method 300 may include determining, using a processing device, at least one dental recommendation based on a processing. At 316, method 300 may include transmitting, using a communication device, at least one dental recommendation to at least one external device. In some embodiments, at least one external device may be associated with at least one patient device. At least one external device may include a smartphone, a tablet, a mobile device, a personal computer, a laptop. In some embodiments, at least one external device may be associated with a second user. A second user may include a dental professional, a health care professional, an expert, an individual, an e-commerce organization, an artificial intelligence system, a researcher, a manufacturer, a business, an application software, a patient portal, a system software, a client device, a processing device. At 318, method 300 may include storing, using a storage device, at least one dental recommendation.

Figure 4:
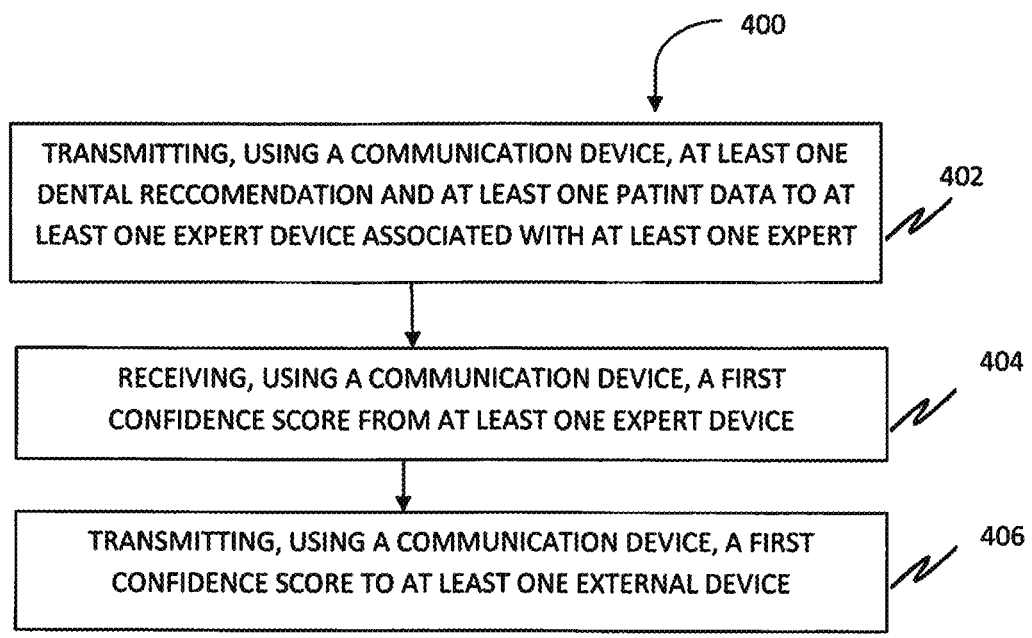
FIG. 4 is a flowchart of a method of obtaining a first confidence score associated with at least one dental recommendation, in accordance with some embodiments.

FIG. 4 is a flowchart of method 400 of obtaining a first confidence score associated with at least one dental recommendation, in accordance with some embodiments. At least one dental recommendation may include at least one of: a real time dental treatment recommendation, a real time dental treatment recommendation for no treatment, a real time dental product recommendation, a real time dental product recommendation for no treatment. At 402, method 400 may include transmitting, using a communication device, at least one dental recommendation and at least one patient data to at least one of: an expert device, a processing device, a patient device associated with at least one expert. At least one expert may include a dental professional, a health care professional, an expert, an individual, an e-commerce organization, an artificial intelligence system, a researcher, a manufacturer, a business, an application software, a patient portal, a system software, a client device, a processing device. At 404, method 400 may include receiving, using a communication device, a first confidence score from at least one of: an expert device, a processing device, a patient device. A first confidence score may include a measure of appreciation. A first confidence score may include a rating, a score. At 406, method 400 may include transmitting, using a communication device, a first confidence score to at least one external device.

Figure 5:
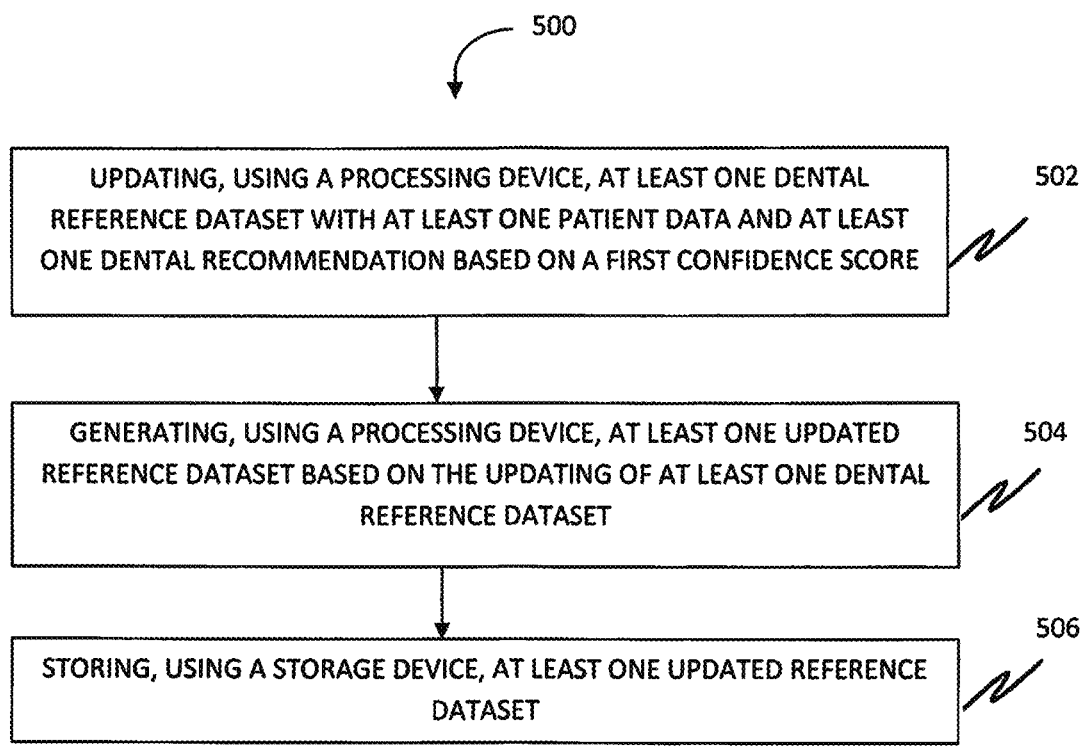
FIG. 5 is a flowchart of a method of obtaining at least one updated reference dataset, in accordance with some embodiments.

FIG. 5 is a flowchart of method 500 of obtaining at least one updated reference dataset, in accordance with some embodiments. At 502, method 500 may include updating, using a processing device, at least one dental reference dataset with at least one patient data and at least one dental recommendation based on a first confidence score. At 504, method 500 may include generating, using a processing device, at least one updated reference dataset based on updating at least one dental reference dataset. At 506, method 500 may include storing, using a storage device and at least one updated reference dataset.

Figure 6:
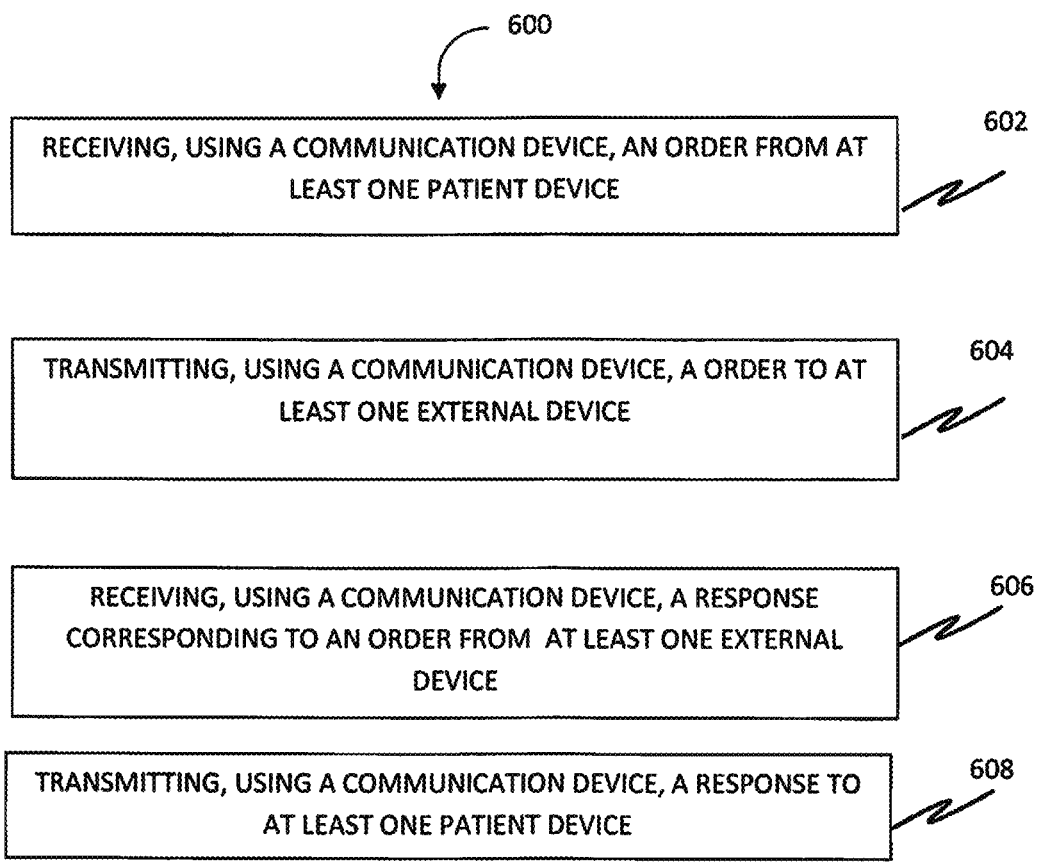
FIG. 6 is a flowchart of a method of processing an order, in accordance with some embodiments.

FIG. 6 is a flowchart of method 600 processing an order, in accordance with some embodiments. An order may be associated with at least one dental recommendation. At 602, method 600 may include receiving, using a communication device, an order from at least one patient device.

At 604, method 600 may include transmitting, using a communication device, an order to at least one external device. At 606, method 600 may include receiving, using a communication device, a response corresponding to an order from at least one external device. At 608, method 600 may include transmitting, using a communication device, a response to at least one patient device.

Figure 7:
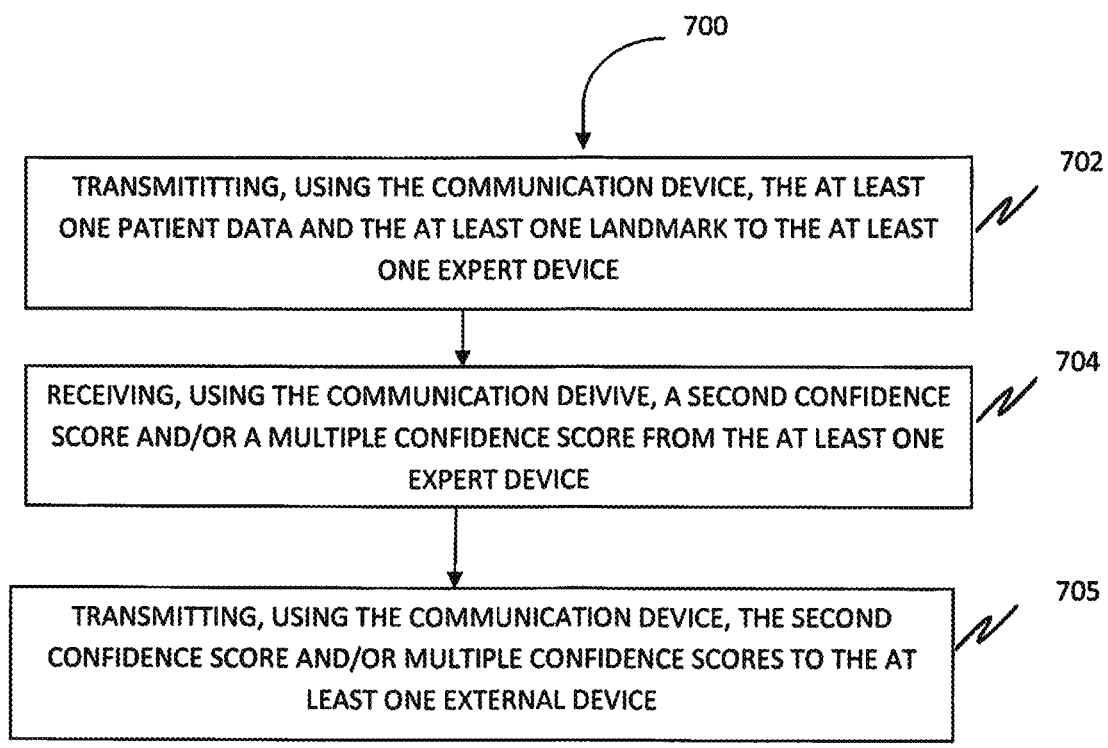
FIG. 7 is a flowchart of a method of obtaining a second confidence score associated with at least one landmark, in accordance with some embodiments.

FIG. 7 is a flowchart of method 700 of obtaining at least one of: a second confidence score, a multiple confidence score associated with at least one landmark, in accordance with some embodiments. At 702, method 700 may include transmitting, using a processing device and/or a communication device, at least one patient data and at least one landmark to at least one of: an expert device, a processing device, a patient device. At 704, method 700 may include receiving, using at least one of: an aggregate server, a communication device at least one of: a second confidence score, a multiple confidence score from at least one of: an expert device, a processing device, a patient device. At least one of: a second confidence score, a multiple confidence score may include a measure of appreciation. At least one of: a second confidence, a multiple confidence score may include a rating and/or a score. At 706, method 700 may include transmitting, using at least one of: a processing device, a communication device at least one of: a second confidence score, a multiple confidence score to at least one external device.

Figure 8:
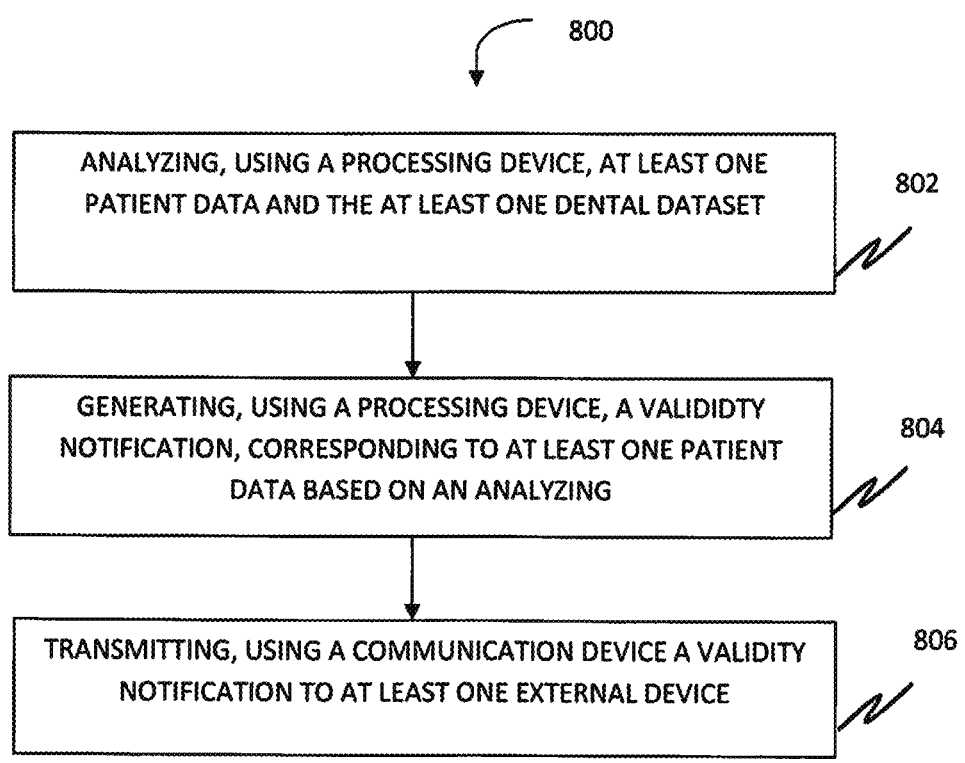
FIG. 8 is a flowchart of a method of obtaining a validity notification corresponding to at least one patient data, in accordance with some embodiments.

FIG. 8 is a flowchart of method 800 of obtaining a validity notification corresponding to at least one patient data, in accordance with some embodiments. At 802, method 800 may include analyzing, using a processing device, at least one patient data and at least one dental dataset. At 804, method 800 may include generating, using a processing device, a validity notification corresponding to at least one patient data based on an analyzing. The validity notification may be associated with a measure of approval of at least one patient data. At 806, method 800 may include transmitting, using a communication device, a validity notification to at least one external device.

Figure 9:
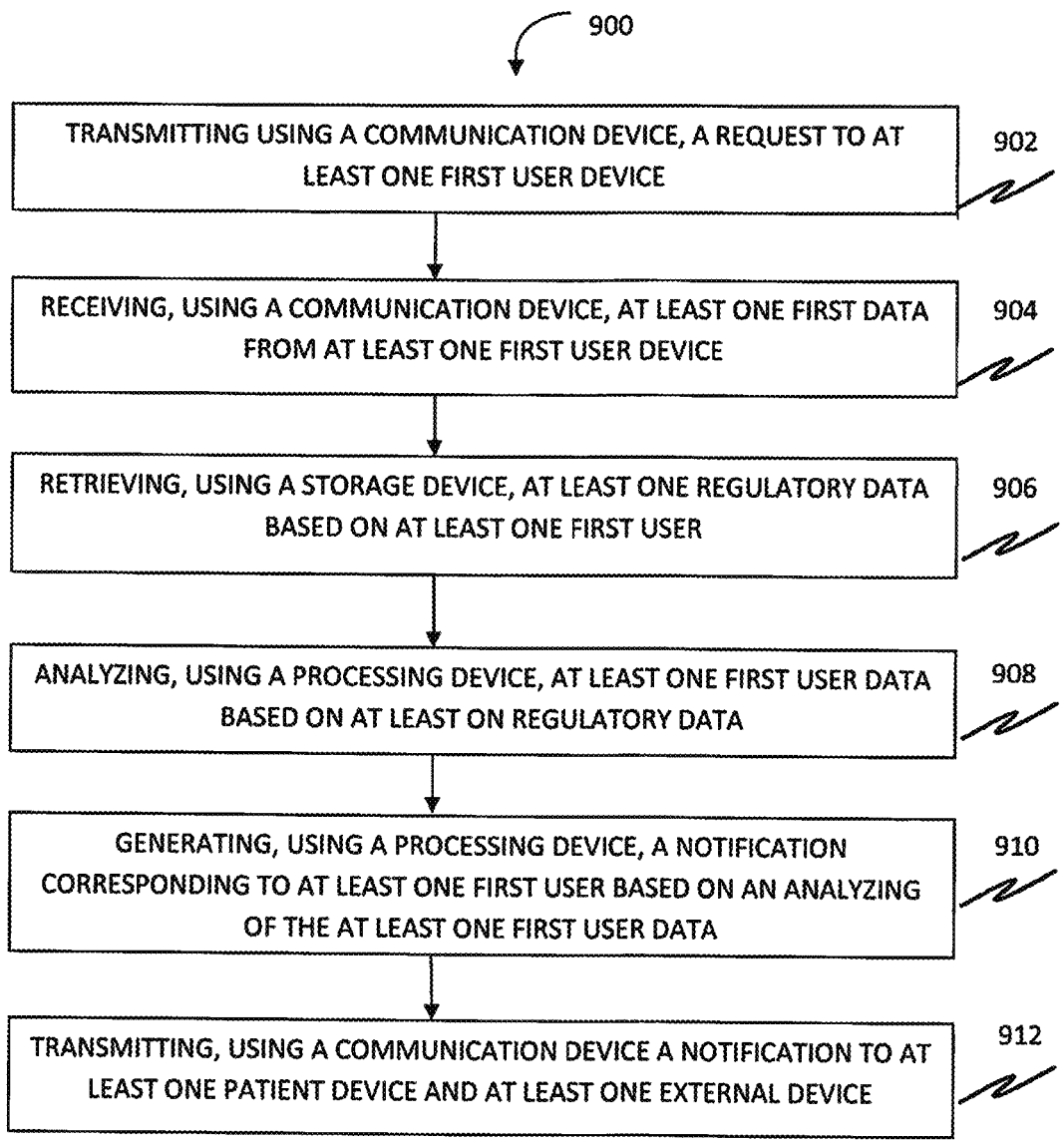
FIG. 9 is a flowchart of a method of obtaining a notification corresponding to at least one first user, in accordance with some embodiments.

FIG. 9 is a flowchart of method 900 of obtaining a notification corresponding to at least one first user, in accordance with some embodiments. At least one external device may include at least one first user device associated with at least one first user. At 902, method 900 may include transmitting, using a communication device, a request to at least one first user device. At 904, method 900 may include receiving, using a communication device, at least one first user data from at least one first user device. At least one first user device may include a smartphone, a tablet, a laptop, a personal computer. At least one first user data may include a certification, a qualification proof, a license number that may be verified. At least one first user may include a dental professional, a healthcare professional, an e-commerce organization, an e-commerce vendor. At 906, method 900 may include retrieving, using a storage device, at least one regulatory data based on at least one first user. At 908, method 900 may include analyzing, using a processing device, at least one first user data based on at least one regulatory data. At 910, method 900 may include generating, using a processing device, a notification corresponding to at least one first user based on an analyzing of at least one first user data. At 912, method 900 may include transmitting, using a communication device, a notification to at least one patient device and at least one external device.

In some embodiments, a method for determining a dental recommendation based on location is disclosed. Accordingly, a method may include a step of analyzing at least one patient data to determine a location data. Accordingly, a method may include a step of analyzing, using a processing device, a location data and at least one dental recommendation. A method may include a step of determining, using a processing device, a first dental recommendation of at least one dental recommendation based on an analyzing of a location data and at least one dental recommendation and a method may include a step of transmitting, using a communication device, a first dental recommendation to at least one external device.

Figure 10:
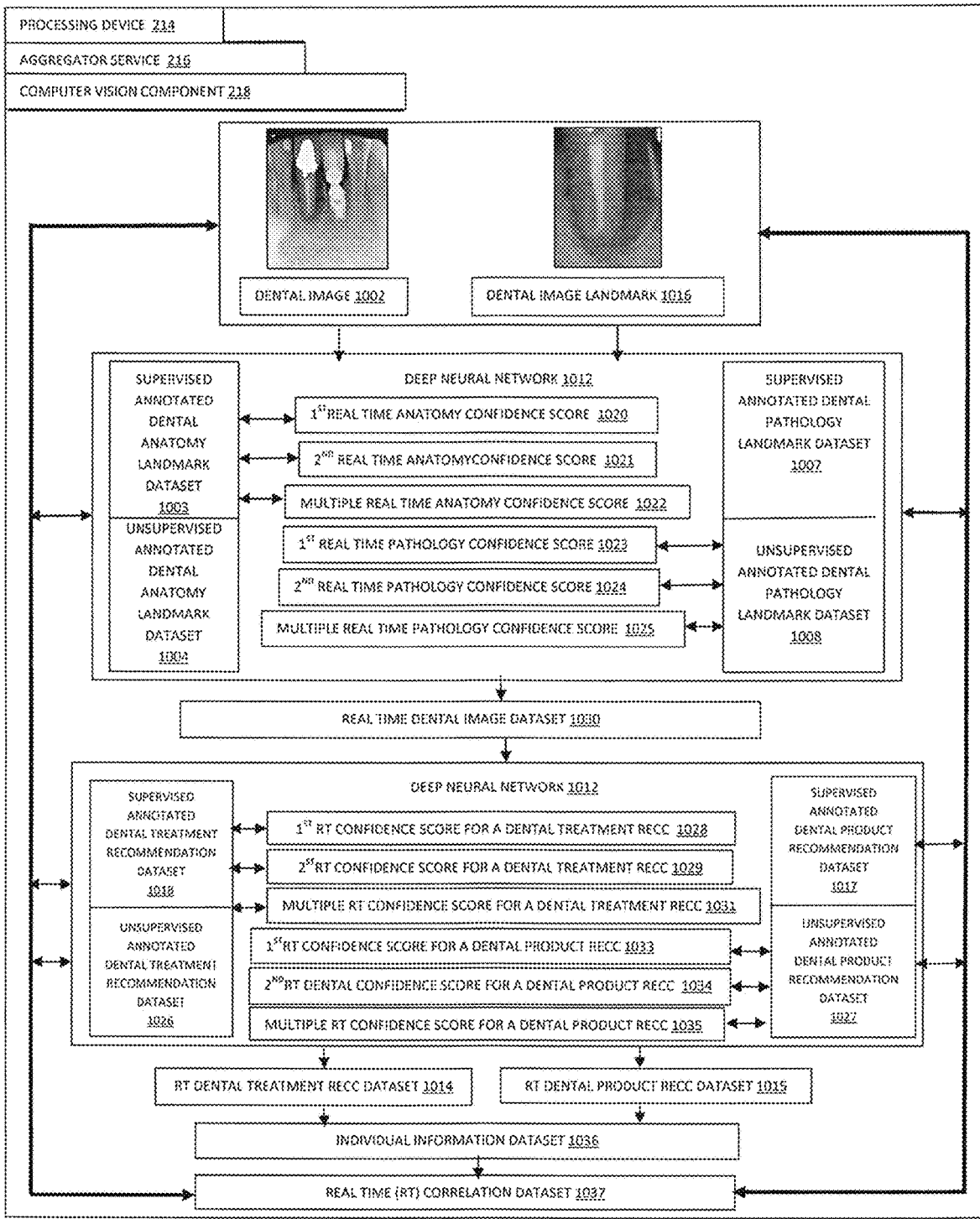
FIG. 10 is a conceptual diagram of a method for facilitating matching and identifying a dental image with a supervised and/or unsupervised annotated deep neural network to produce a real time correlation dataset, in accordance with some embodiments.

FIG. 10 is a conceptual diagram demonstrating the use of at least one of: a machine learning, a deep learning to process at least one of: a dental image 1002, a dental image landmark 1016 with a deep neural network 1012 to produce a real time correlation dataset 1037. The system may instruct an aggregate server 214 to process an aggregator 216 to utilize a computer vision component 218 to process at least one of: a dental image 1002, a dental image landmark 1016 with at least one of: a supervised annotated dental anatomy landmark dataset 1003, an unsupervised annotated dental anatomy landmark dataset 1004 to produce at least one of: a first real time anatomy confidence score 1020, a second real time anatomy confidence score 1021, a multiple real time anatomy confidence score 1022 and provide to a real time dental image dataset 1030. The process may also process at least one of: a dental image1002, a dental image landmark 1016 with at least one of: a supervised annotated dental pathology landmark dataset, an unsupervised annotated dental pathology landmark dataset 1008 to produce at least one of: a first real time pathology confidence score 1023, a second real time pathology confidence score 1024, a multiple real time pathology confidence score 1025 and provide to a real time dental image dataset 1030.

The real time dental image dataset 1030 may be processed with a deep neural network to at least one of: a supervised annotated dental treatment recommendation dataset, an unsupervised annotated dental treatment recommendation dataset 1026 to produce at least one of: a first real time confidence score for a dental treatment recommendation 1028, a second real time confidence score for a dental treatment recommendation 1029, a multiple real time confidence score for a dental treatment recommendation 1031 and provide to a real time dental treatment recommendation dataset 1014. Wherein, a real time dental treatment recommendation dataset 1014 contains at least one of: a real time dental treatment recommendation, a real time dental treatment recommendation for no treatment. Further, the real time dental image dataset 1030 and the real time dental treatment dataset 1014 may be processed with a deep neural network to at least one of: a supervised annotated dental product recommendation dataset, an unsupervised annotated dental product recommendation dataset 1027 to produce at least one of: a first real time confidence score for a dental product recommendation 1033, a second real time confidence score for a dental product recommendation 1034, a multiple real time confidence score for a dental product recommendation 1035 and provide to a real time dental product recommendation dataset 1015. Wherein, a real time dental product recommendation dataset 1015 contains at least one of: a real time dental product recommendation, a real time dental product recommendation for no product.

Correlate at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product with an individual information dataset 1036 and provide to a real time correlation dataset 1037. Wherein, an individual information dataset 1036 includes at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a change of location, a biometric measurement, a biometric sensor measurement, a genetic dataset, an internet browsing history, a dataset. Further, FIG. 10 shows at least one of: a processing device, an aggregator is configured to execute an instruction in any order and the processing server is configured to omit an instruction in any order. Wherein an instruction may include one of: a match, an identify, a score, a rule, a train, a process, an exchange, a transfer, a purchase, a sell an analyze, an order.

Figure 11:
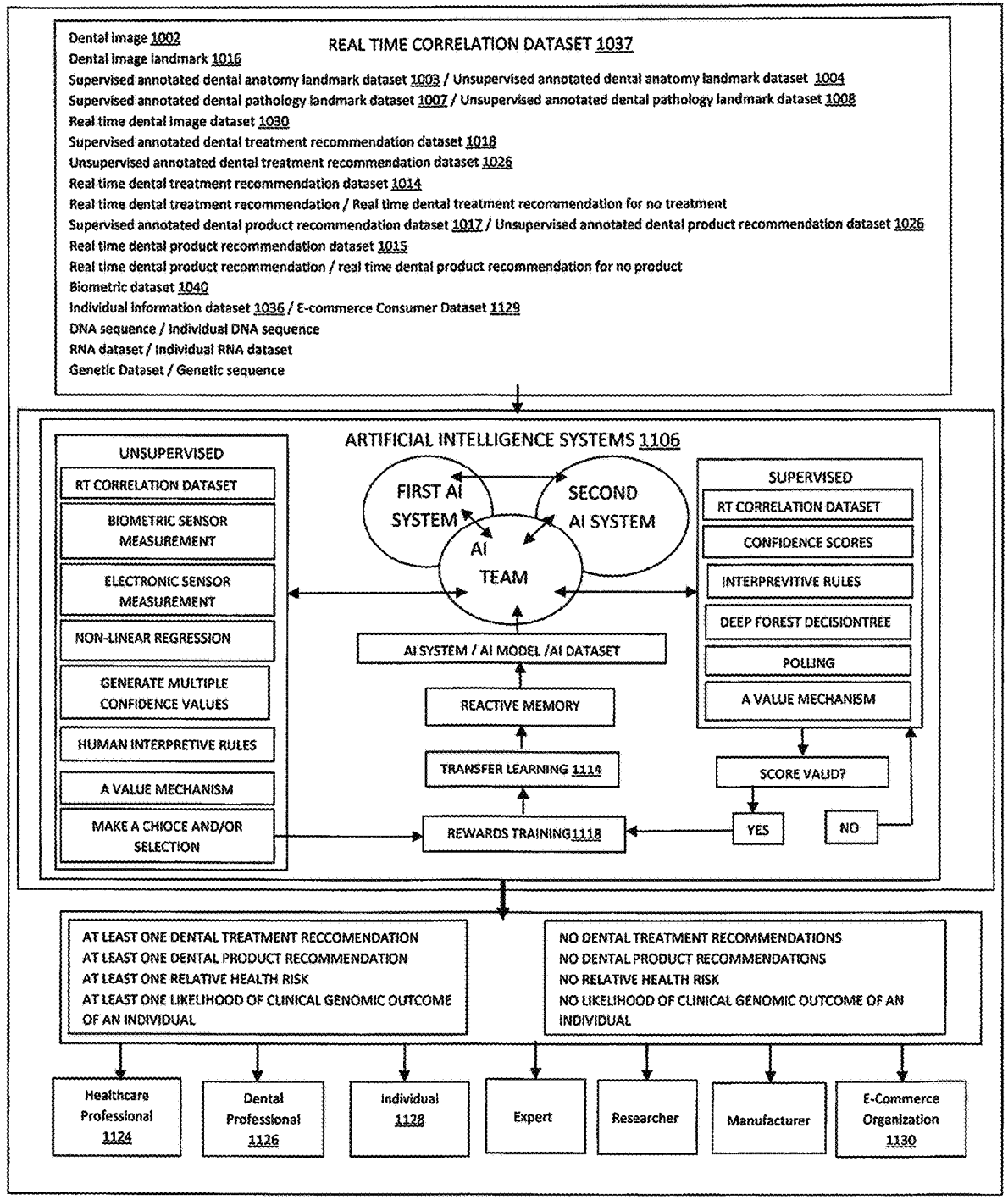
FIG. 11 is a conceptual diagram for processing a real time correlation dataset with artificial intelligence systems to produce a polling from at least one of: a first artificial intelligence system, a second artificial intelligence system, a team of artificial intelligence systems to produce at least one of: a real time dental treatment recommendation, a real time dental treatment recommendation for no treatment, a real time dental product recommendation, a real time dental product recommendation for no product.

FIG. 11 is a conceptual diagram for processing a real time correlation dataset 1037 with artificial intelligence systems 1106 to produce a polling from at least one of: a first artificial intelligence system, a second artificial intelligence system, a team of artificial intelligence systems to produce at least one of: a real time dental treatment recommendation, a real time dental treatment recommendation for no treatment, a real time dental product recommendation, a real time dental product recommendation for no product. Wherein, the real time correlation dataset 1037 includes at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040.

The real time correlation dataset is provided to an artificial intelligence system 1106. Wherein, an artificial intelligence may also be referred to as "AI" in the embodiment of the invention and in the figures. Artificial intelligence systems may include using at least one of: an artificial intelligence system, an artificial intelligence dataset, an artificial intelligence model. An artificial intelligence system, an artificial intelligence dataset, an artificial intelligence model may work individually or as a team in any order or combination. At least one of: an artificial intelligence system 1106, an artificial intelligence dataset, an artificial intelligence model does not necessarily imply sentient intelligence but may act as an interface of human interpretation rules and training that are provided to at least one of: a first artificial intelligence system, a second artificial intelligence system, a team of artificial intelligence systems.

The real time correlation dataset 1037 is provided to the artificial intelligence system 1106 may then be provided to at least one of: an artificial intelligence system, an artificial intelligence dataset, an artificial intelligence model and may be processed by supervised processing. Supervised processing may use at least one of: a correlation dataset 1037, a confidence score, an interpretation rule, a deep forest decision tree, a polling, a value mechanism. The supervised processing may be provided to an artificial intelligence system to generate a polling to produce at least one of: a real time dental treatment recommendation dataset, a real time dental treatment recommendation, a real time dental treatment recommendation for no treatment, a real time dental product recommendation dataset, a real time dental product recommendation, a real time dental product recommendation for no product. Further, the supervised processing may be provided to the artificial intelligence system 1106 and may be provided to at least one of: an artificial intelligence system, an artificial intelligence dataset, an artificial intelligence model.

An unsupervised processing may use at least one of: a correlation dataset 1037, a biometric sensor measurement, an electronic sensor measurement, a non-linear regression, generate multiple confidence values, a confidence score, a human interpretation rule, a value mechanism, make a choice, make a selection. An unsupervised processing may be provided to the artificial intelligence systems to generate a polling to produce at least one of: a real time dental treatment recommendation dataset, a real time dental treatment recommendation, a real time dental treatment recommendation for no treatment, a real time dental product recommendation dataset, a real time dental product recommendation, a real time dental product recommendation for no product. Further, the unsupervised processing may be provided to the artificial intelligence system 1106 and may be provided to at least one of: an artificial intelligence system, an artificial intelligence dataset, an artificial intelligence model.

The supervised and/or unsupervised processing may also generate a real time confidence score poll from at least one of: a first artificial intelligence system, a second artificial intelligence system, a team of artificial intelligence systems based on human interpretation rules and training to at least one of: select, instruct at least one of: a real time dental treatment recommendation, a real time dental treatment recommendation for no treatment, a real time dental product recommendation, a real time dental product recommendation for no product and provide to at least one of: a health care professional 1124, a dental professional 1126, an expert, an individual 1128, an e-commerce organization 1130, a researcher, a manufacturer, a business, an application software, a patient portal, a system software, a client device, a processing device.

An artificial intelligence system 1006 may use rewards training 1118 or a transfer learning 1114 based on human interpretation rules and training to generate a polling from at least one of: a first artificial intelligence system, a second artificial intelligence system, a team of artificial intelligence systems. An artificial intelligence system 1106 may generate a real time confidence score poll for at least one of: a first artificial intelligence system, a second artificial intelligence system, a team of artificial intelligence systems based on human interpretation rules and training to at least one of: select, instruct at least one of: a real time dental treatment recommendation, a real time dental treatment recommendation for no treatment, a real time dental product recommendation, a real time product recommendation for no product and provide to at least one of: a health care professional 1124, a dental professional 1126, an expert, an individual 1128, an e-commerce organization 1130, a researcher, a manufacturer, a business, an application software, a patient portal, a system software, a client device, a processing device.

At least one of: a dental image 1002, a dental image landmark 1016 may be obtained from at least one of: a digital x-ray, a digital image, a cell phone captured image, a photographic image, a toothbrush with imaging device, a toothbrush with imaging device being a camera, a film based x-ray, a digitally scanned x-ray, a digitally captured x-ray, an intraoral scanner, a scintillator technology based image, a trans-illumination image, a fluorescence technology based image, a blue fluorescence technology based image, a laser based technology based image, a magnetic resonance image (MRI), a computed tomography (CT) scan based image, a cone beam computed tomography (CBCT) image. Further, a dental professional 1126, a health care professional 1124, an expert, an individual 1128, an e-commerce organization 1130, a researcher, a manufacturer, a business, an application software, a patient portal, a system software, a client device, a processing device may utilize an image capture device or a data storage device to obtain at least one of: a dental image 1002, a dental image landmark 1016 wherein the image capture device includes one or more of: an image capture device, an x-ray equipment, a digital camera, an intraoral camera, a cell phone camera, an intraoral scanner, a scintillator counter, an indirect or direct flat panel detector (FPD), a charged couple device (CCD), a phosphor plate radiography device, a picture archiving and communication system (PACS), a photo-stimulable phosphor (PSP) device, a wireless complementary metal—oxide—semiconductor (CMOS) device. Further at least one of: a dental image 108, a dental image landmark, an image, an image landmark may be obtained from at least one of: Facebook, Inc., Instagram, Snap Inc., Apple Inc., Microsoft, Inc., Alphabet, Inc., Snowflake, Inc., Datadog, Inc., Amazon.com, Inc., Align Technology Inc., Smile Direct Club, Inc., Cube Click, Inc.

An example of a dental professional 1126 or a health care professional 1124 includes a dentist, a hygienist, a dental assistant, a dental staff member, a medical staff member, a dental laboratory technician, a physician, a nurse, a medical technician, a veterinarian, a veterinarian professional, a licensed professional. An example of an individual 1128 includes an individual, a guardian, an employee. An example of e-commerce organization 1130 includes a business, a business entity, a business owner, an employer, a wholesaler, a retailer, a group, a research entity, a law enforcement entity, a public administration entity, an administrator, an administrator entity, a governing agency, a bioinformatics service, an insurance company, a cloud based storage service. An individual 1128 may provide at least one of: a dental image 1002, a dental image landmark 1016 with an image capture device or a data storage device wherein the capture image device includes at least one of: a camera, a digital camera, a cell phone camera, a photographic image, a toothbrush with imaging device, a toothbrush with imaging device being a camera, an intraoral camera.

Train the processing device 214 to use at least one of: machine learning, deep learning to match and identify at least one of: a dental image 1002, a dental image landmark 1016 to at least one of: a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008 with a deep neural network 1012 with at least one of: a machine learning system, a deep learning system. Each deep neural network 1012 may learn to detect different dental image landmarks of a dental image 1002 and match and identify to at least one of: a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008 to produce at least one of: a first real time confidence score of a dental anatomy landmark 1020, first real time confidence score of a dental pathology landmark 1023, a second real time confidence score of a dental anatomy landmark 1021, a second real time confidence score of a dental pathology landmark 1024, a multiple real time confidence score 1022 of a dental anatomy landmark, a multiple real time confidence score of a dental pathology landmark 1025 and provide a real time confidence score to a real time dental image dataset 1030. A supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008 may be at least one of: obtained, annotated from at least one of: a dental professional 1126, a health care professional 1124, an expert, an individual 1128, an e-commerce organization 1130, an artificial intelligence system, 1106 a researcher, a manufacturer, a business, an application software, a patient portal, a system software, a client device, a processing device.

The process may be followed by training an aggregate server to use at least one of: machine learning, deep learning to match and identify a real time confidence score for a real time dental image dataset 1030 to at least one of: a supervised annotated dental treatment recommendation dataset, an unsupervised annotated dental treatment recommendation dataset 1026 to produce at least one of: a first real time confidence score for a real time dental treatment recommendation 1028, a second real time confidence score for a real time dental treatment recommendation 1029, a multiple real time confidence score for a real time dental treatment recommendation 1031 and provide a real time confidence score to a real time dental treatment recommendation dataset 1014. At least one of: a supervised annotated dental treatment recommendation dataset 1018, an unsupervised annotated dental treatment recommendation dataset 1026 may be at least one of: obtained, annotated from at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device.

The process may continue by training an aggregate server to use at least one of: machine learning, deep learning to match and identify at least one of: a real time dental image dataset 1030, a real time dental treatment recommendation dataset 1014 to at least one of: a supervised annotated dental product recommendation dataset 1017, an unsupervised annotated dental product recommendation dataset 1027 to produce at least one of: a first real time confidence score for a dental product recommendation 1033, a second real time confidence score for a dental product recommendation 1034, a multiple real time confidence score for a product recommendation 1035 and provide a real time confidence score to a real time dental product recommendation dataset 1015. At least one of: supervised annotated dental product recommendation 1017, an unsupervised annotated dental product recommendation dataset 1027 may be at least one of: obtained, annotated from at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device. An example of a real time dental product recommendation may include recommending a specific orthodontic aligner or a manufacturer for an orthodontic aligner fabrication. Another example of a real time dental product recommendation may include a specific dental implant or a specific dental implant size based on a dental image 1002. Further examples of product dental product recommendations may include no product, at least one product, a brand of dental crown, a dental laboratory, a membrane, a graft, a screw, a composite, an amalgam, a cement, a luting agent, a gutta percha, a restorative material, an endodontic restorative material, a temporary restorative material, an antimicrobial agent, an antibiotic agent, a medication, a preventive product, a preventive material, an impression material, a dental instrument.

Correlate or associate at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, a biometric dataset 1040 with an individual information dataset 1036 to produce a real time correlation dataset 1037. Wherein, an individual information dataset 1036 may include at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a change of location, a biometric measurement, a biometric sensor measurement, a genetic dataset, an internet browsing history, a dataset.

Correlate or associate at least one of: a real time dental treatment recommendation dataset 1014, a real time dental treatment recommendation, a real time dental treatment recommendation for no treatment, a real time dental product recommendation dataset 1015, a real time dental product recommendation, a real time dental product recommendation for no product with an individual information dataset 1036 and provide to a referral system. Wherein, a referral system may refer to at least one of: a dental professional 1126, a dental specialist, a health care professional 1124, a health care specialist, a dentist, a dental specialist, a hygienist, a dental assistant, a dental staff member, a dental laboratory technician, a physician, a physician specialist, a nurse, a medical technician, an veterinarian, a veterinarian professional.

At least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a real time correlation dataset 1037 may be processed with at least one of: an artificial intelligence system 1106, an artificial intelligence model, an artificial intelligence dataset that comprises at least one of: a deep neural network 1012, a machine learning model, a recurrent neural network model, at least one deep neural layer, a deep forest decision tree, an independent neural network, an artificial intelligence platform.

Provide a plurality of human interpretation rules based on at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 to at least one of: a first artificial intelligence system, a second artificial intelligence system, 1106, a team of artificial intelligence systems.

Train with human interpretation rules at least one of: a first artificial intelligence system, a second artificial intelligence system, a team of artificial intelligence systems to at least one of: choose, select, opt at least one of: a real time dental image dataset 1030, a real time dental treatment recommendation dataset 1014, a real time dental treatment recommendation, a real time dental treatment recommendation for no treatment, a real dental product recommendation dataset 1015, a real time dental product recommendation, a real time dental product recommendation for no product, an individual information dataset 1036, a biometric dataset 1040, a real time correlation dataset 1037 based on at least one human interpretation rule being met and provide to at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device.

Generate a real time confidence score poll from at least one of: a first artificial intelligence system, a second artificial intelligence system, a team of artificial intelligence systems to at least one of: select, choose, opt to instruct at least one of: a real time dental treatment recommendation, a real time dental treatment recommendation for no treatment, a real time dental product recommendation, a real time dental product recommendation for no product based on at least one human interpretation rule or training being met and provide in real time to at least one of: a dental professional 1126, a health care professional 1124, an expert, an individual 1128, an e-commerce organization 1130, an artificial intelligence system, a researcher, a manufacturer, a business, an application software, a patient portal, a system software, a client device, a processing device.

At least one of: an artificial intelligence system, an artificial intelligence model, an artificial intelligence dataset may match may process and store patient compliance factors by querying dental software data fields by at least one of: an insurance maximum, a remaining insurance benefit, a missed appointment, a rescheduled appointment. In another scenario predetermined questions may be queried to profile a patient compliance by at least one of: a dental phobia, a financial challenge, a lifestyle change, a business plan, a travel plan, an illness, an injury. An artificial intelligence system, an artificial intelligence dataset, an artificial intelligence model may identify individual financial obstacles to treatment and may suggest a specific third party financing company. At least one of: an artificial intelligence system, an artificial intelligence model, an artificial intelligence dataset may compare treatment success and produce a real time confidence score for at least one of: a real time dental treatment recommendation, a real time dental treatment recommendation for no treatment, a real time dental product recommendation, a real time dental product recommendation for no product based on a patient compliance factor which may include at least one of: a number of individual visits, a number of broken appointments, a failure to complete treatment rate, an ASA grade, a smoker, a diabetic, a biologic medication and provide to at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device. Based on predetermined questions, an artificial intelligence system 1106, an artificial intelligence model, an artificial intelligence dataset may also suggest sedation dentistry for an individual 1128.

At least one of: an artificial intelligence system 1106, an artificial intelligence model, an artificial intelligence dataset may offer at least one of: a real time dental treatment recommendation, a real time dental treatment recommendation for no treatment, a real time dental product recommendation, a real time dental product recommendation for no product to at least one of: a specialist, a dental professional 1126, a health care professional 1124, an expert, an individual 1128, an e-commerce organization 1130, an e-commerce provider, an artificial intelligence system 1106, a researcher, a manufacturer, a business, an application software, a patient portal, a system software, a client device, a processing device.

At least one of: an artificial intelligence system, an artificial intelligence model, an artificial intelligence dataset may buy or sell at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 over a communication network such as the internet. Further, at least one of: an artificial intelligence system, an artificial intelligence dataset, an artificial intelligence model may make a referral based on a geographic location such as a Global Position System (GPS) or Global Navigation System (GLONASS). In addition, at least one of: an artificial intelligence system, an artificial intelligence model, an artificial intelligence dataset may recognize when a patient has moved or changed address location and recommend new dentists and dental specialists based on a geographic location such as a Global Position System (GPS) or Global Navigation System (GLONASS).

A processing device 214 may be configured to use at least one of: machine learning, deep learning electronic sensory measurements of at least one of: a vision, a sound, a touch, a smell, a taste biometric sensor, a sensor biometric sensor, a sensor and may be correlated or associated with at least one of: a dental image 1002, a dental image landmark 1016. An individual may provide electronic sensory information from a client device, wherein a client device includes at least one of: a server, a desktop computer, a workstation, a laptop computer, a cell phone, a tablet, a mobile device, a cloud based storage service. Further, hidden or obvious electronic sensors may monitor biometric sensor measurements in at least one of: a dental office, a medical office, a veterinarian office, a law enforcement facility, a professional facility, a business facility, a research facility, an e-commerce organization 1130 and at least one of: a processing device 214, a communication device may correlated or associate hidden or obvious biometric sensor measurements with at least one of: a dental image 1002, a dental image landmark 1016. Electronic sensors 116 may include at least one of: a sensor, a biometric sensor, a biometric measurement sensor which may include at least one of: a vision sensor, a camera, a computer vision which may measure at least one of: a fidgeting, a stillness, an eye movement, an alertness, a disinterest, a fear, a gesture. A sound sensor or a microphone sensor may measure at least one of: a laughter, a silence, a moaning, a groaning, a panting, a cadence, a pitch. A touch sensor such as a figure print sensor may measure at least one of: a body temperature, a sweating, a heartbeat. A smell sensor such as a halitosis meter may measure at least one of: a bad breath, a body odor. A taste receptor such as an electronic tongue or a digital taste interface may measure at least one of: a salt, a sweet, a sour, a spicy, a wetness, a dryness. Biometric sensory measurements may be correlated or associated with location with a Global Position System (GPS) or Global Navigation System (GLONASS). Electronic sensory measurements may also be correlated or associated with a timing device such as a real clock.

Human interpretation rules and training of electronic sensory measurements or biometric sensor measurements may be provided to at least one of: an intelligence system, an artificial intelligence dataset, an artificial intelligence model. At least one of: an artificial intelligence system, an artificial intelligence dataset, an artificial intelligence model may correlate an individual's electronic sensor measurements or an individual's biometric sensor measurements (e.g., vision sensor, computer vision, sound sensors, microphones, touch sensors, pressure sensors, smell sensors, halitosis meters, taste sensors, electric tongue, biometric sensor, a sensor) to at least one of: an individual information dataset 1036, correlation dataset 1037 to produce a biometric dataset 1040 to at least one of: choose, select, opt at least one of: a real time dental treatment recommendation, a real time dental treatment recommendation for no treatment, a real time dental product recommendation, a real time dental product recommendation for no product based on at least one of: an dental image 1002, a dental image landmark 1016 and provided to at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device.

At least one of: an artificial intelligence system 1106, an artificial intelligence model, an artificial intelligence dataset may verify the identity of an individual 1128 from his or hers real time correlation dataset 1037 and provide to a government agency such as Home Land Security. Further, at least one of: a dental image, a dental image landmark, an image, an image landmark, an insurance claim, an insurance data may be verified by at least one of: a dental professional 1126, a health care professional 1124, an expert, an e-commerce consumer, an individual 1128, an e-commerce organization 1130, a business, an artificial intelligence system 1106, a researcher, a manufacturer, a business, an application software, a patient portal, a system software, a client device, a processing device with a verification of least one of: an insignia, a mark, a code, an indicia, a logo, a non visual of the verification may be at least one of: associate, visually placed on at least one of: a dental image, a dental image landmark, an image, an image landmark, an insurance claim, an insurance data. At least one of: a dental image, a dental image landmark, an image, an image landmark, an insurance claim, an insurance data may be proof of verification and allowance by an e-commerce, an individual for digital processing with at least one of: an insignia, a mark, a code, an indicia, a logo, a non visual code.

The process may select at least one of: an artificial intelligence system, an artificial intelligence model, an artificial intelligence dataset to identify human remains by comparing at least one of: a deceased dental image 1002, a deceased dental image landmark 1016 with a predeceased dataset of at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a correlation dataset 1037 and provide to a government agency. Further, at least one of: a dental professional 1126, a health care professional 1124, an expert, an individual 1128, an e-commerce organization 1130, an artificial intelligence system 1106, a researcher, a manufacturer, a business, an application software, a patient portal, a system software, an artificial intelligence system 1106, an artificial intelligence model, an artificial intelligence dataset may identify or correlate a patient's geographic dental visit movements with a real time correlation dataset 1037. This geographic dental visit movement or location may be provided to a government agency such as Child Protective Services (CPS) or the National Center for Missing & Exploited Children (NCMEC) to track abducted children. A processing device 214 may use an artificial intelligence mechanism to process at least one of: a dental image 1002, a dental image landmark 1016 with a natural language processing [NLP] dataset. Wherein, a natural language dataset may include at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037.

The supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 are configured to continually merge and correlate additional annotated information from at least one of: a dental professional 1126, a health care professional 1124, an expert, an individual 1128, an e-commerce organization 1130, an artificial intelligence system, 1106 a researcher, a manufacturer, a business, an application software, a patient portal, a system software, a client device, a processing device. Additionally, at least one of: a dental image 1002, a dental image landmark 1016 may be processed with at least one of: a supervised learning, unsupervised learning, rewards training 1118, transfer learning 1114, confidence values, confidence scores, reactive memory, non reactive memory, a memory of dataset, a system of artificial intelligence with memory. At least one of: real time dental image dataset 1030, a real time dental treatment recommendation dataset 1014, a real time dental product recommendation dataset 1015 may be associated with a treatment confidence score to produce a reward training 1118 or a transfer learning value for at least one of: an artificial intelligence system 1106, an artificial intelligence model, an artificial intelligence dataset. The confidence score for rewards training 1118 or transfer learning of treatment recommendations or no treatment options and product recommendations or no product recommendations may be provided to at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device. Further, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 may be configured to identify and correct for missing information.

A processing device 214 is configured to execute an aggregator 216 to exchange at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 with a client device. Wherein, a client device includes at least one of: a server, a desktop computer, a workstation, a laptop computer, a cell phone, a tablet, a mobile device, a cloud based storage service.

A processing device is configured to process at least one of: a dental image 1002, a dental image landmark 1016 with at least one of: (a sliding window component configured to analyze at least one of: a dental image 1002, a dental image landmark 1016), (a multiple grid component to divide and analyze at least one of: a dental image 1002, a dental image landmark 1016), (a bounding box component configured to analyze at least one of: a dental image 1002, a dental image landmark 1016), (a bounding box component configured to generate an image confidence score for at least one of: dental image 1002, a dental image landmark 1016), an image classification component configured to generate a dental image confidence score, an object classification component configured to generate a dental object confidence score, a value mechanism component configured to generate a treatment confidence score, a value mechanism component configured to generate a dental product confidence score, a value mechanism component configured to generate a real time dental treatment recommendation, a value mechanism component configured to generate a real time dental product recommendation, (a semantic segmentation component configured to generate a semantic segmentation of at least one of: a dental image 1002, a dental image landmark 1016), (an instance segmentation component configured to generate an instance segmentation of at least one of: a dental image 1002, a dental image landmark 1016), (a supervised learning component configured to annotate at least one of: a dental image 1002, a dental image landmark 1016), (an unsupervised learning component configured to annotate at least one of: a dental image 1002, a dental image landmark 1016), a recurrent neural network component (RNN) configured to analyze a dataset, an independent neural network component (INDRNN) configured to analyze a dataset, a deep forest decision tree configured to analyze a dataset, a processor configured for a system of memory of dataset, a processor configured for an artificial intelligence system 1106 with memory, a processor configured for a system of reactive memory, a processor configured for a system of non reactive memory, a processor configured for a system of rewards training 1118, a processor configured for a system of transfer learning 1114, (a processor configured with an object tracking mechanism configured to track objects in at least one of: a dental image 1002, a dental image landmark 1016), a processor configured for natural language processing (NLP).

A processor configured to perform at least one of: non-linear regression, exponential powers laws, a geometric series, binomial distribution. A processor configured to upload or download at least one of: an exchange, a transmission, a storage of a dataset with at least one of: a server, a desktop computer, a workstation, a laptop computer, a cell phone, a tablet, a mobile device, a cloud based storage service. A processor configured for at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device to process a transaction of at least one of: an exchange, a transfer, a buy, a sell at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 wherein, a transaction is at least one of: business to business (B2B), business to consumer (B2C), consumer to business (C2B), consumer to consumer (C2C), business to administration (B2A), consumer to administration (C2A) in exchange for at least one of: a currency, a data, a discount, a product, a good, a software, an application, an advertisement. Further, an e-commerce transaction includes at least one of: business to business (B2B), business to consumer (B2C), consumer to business (C2B), consumer to consumer (C2C), business to administration (B2A), consumer to administration (C2A).

A processing device 214 is configured to execute an aggregator 216 to compensate for distorted or missing image information. A processing device 214 is configured to execute an aggregator 216 to match and identify at least one of: a dental image 1002, a dental image landmark 1016 with at least one deep neural network 1012 layer with at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037. Further, the processing device 214 is configured to execute an aggregator 216, wherein at least one of: a dental image 1002, a dental image landmark 1016 is processed with a deep neural network layer 1012 and is configured to match and identify at least one of: a dental image anatomy, a dental image pathology, a dental treatment, a dental product recommendation, an individual information dataset 1036, a biometric sensor measurement, a real time dental treatment recommendation, a real time dental treatment recommendation for no treatment, a real time dental product recommendation, a real time dental product recommendation for no product, a real time correlation dataset 1037.

A processing device 214 is configured to execute an aggregator 216 to produce at least one of: a real time dental treatment recommendation, a real time dental treatment recommendation for no treatment, a real time dental product recommendation, a real time dental product recommendation for no product for at least one of: a dental professional 1126, a health care professional 1124, an expert, an individual 1128, an e-commerce organization 1130, a researcher, an artificial intelligence system 1106, a researcher, a manufacturer, a business, an application software, a patient portal, a system software, a client device, a processing device. Provide or store at least one of: a real time dental treatment recommendation, a real time dental treatment recommendation for no treatment, a real time dental product recommendation, a real time dental product recommendation for no product to a client device, wherein a client device includes at least one of: a server, a desktop computer, a workstation, a laptop computer, a cell phone, a tablet, a mobile device, a cloud based storage service.

A processing device 214 is configured to execute an aggregator 216 to provide at least one of: a diagnostic treatment aid, a treatment demonstration aid to at least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device. The processing device 214 may be configured to represent at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 for display as at least one of: a number, a percentage, a percent, a proportion, a ratio, a graph, a color, an image, a score, a grade, a count, a rate, an average, a figure, an outline, an area, a shading. At least one of: a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device may use at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 as a demonstration aid.

A processing device 214 is configured to provide dental recommendations for e-commerce based on image processing. The processing device 214 comprising at least one of: a computer vision 218 component configured to analyze at least one of: a dental image 1002, a dental image landmark 1016 and a memory configured to store instructions associated with an aggregator 216. A processor configured to unidirectional or bidirectional exchange at least one of: a dental image 1002, a dental image landmark 1016, a real time dental image dataset 1030, a real time dental treatment recommendation dataset 1014, a real time dental treatment recommendation, a real time dental treatment recommendation for no treatment, a real time dental product recommendation dataset 1015, a real time dental product recommendation, a real time dental product recommendation for no product, an individual information dataset 1036, a biometric dataset 1040, a real time correlation dataset 1037, a dataset with a mobile device or a cell phone. A processor coupled to a computer vision 218 component and the memory. The processor executing the instructions associated with the processing service 216. The processing service 216 includes an image processing engine configured to process or receive at least one of: a dental image 1002, a dental image landmark 1016 and identify and correct a discrepancy between at least one of: a dental image 1002, a dental image landmark 1016. Further, an image processing engine may match and identify at least one of: a dental image 1002, a dental image landmark 1016 to a supervised annotated dental anatomy landmark dataset 1003, an unsupervised annotated dental anatomy landmark dataset, a supervised annotated dental pathology landmark dataset 1007, an unsupervised annotated dental pathology landmark dataset 1008 to generate at least one of: a real time confidence score of a dental anatomy landmark, a real time confidence score of a dental pathology landmark and provide to a real time dental image dataset 1030. Match and identify a real time dental image dataset 1030 to at least one of: a supervised annotated dental treatment recommendation dataset 1018, an unsupervised annotated dental treatment recommendation dataset 1026 to generate a real time confidence score for a real time dental treatment recommendation and provide to a real time dental treatment recommendation dataset 1014. Further, an image processing engine may match and identify at least one of: a real time dental image dataset 1030, a real time dental treatment recommendation dataset 1014 to at least one of: a supervised annotated dental product recommendation dataset 1017, an unsupervised annotated dental product recommendation dataset 1027 to generate a real time confidence score for a dental product recommendation and provide to a real time dental product recommendation dataset 1015.

Further, an image processing engine is configured to process or correlate at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, a biometric dataset 1040 to an individual information dataset 1036, wherein an individual information dataset 1036 includes at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a change of location, a biometric measurement, a biometric sensor measurement, a genetic dataset, an internet browsing history, a dataset and provide to a real time correlation dataset 1037. Process at least one of: an individual information dataset 1036, a real time correlation dataset 1037, a real time dental treatment recommendation dataset 1014, a real time dental product recommendation dataset 1015 to a referral system and provide to at least one of: a dental professional 1126, a dental specialist, a health care professional 1124, a health care specialist, a dentist, a dental specialist, a hygienist, a dental assistant, a dental staff member, a medical staff member, a dental laboratory technician, a physician, a physician specialist, a nurse, a medical technician, a veterinarian, a veterinarian professional, a licensed processional. Generate a demonstration aid of at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 and provide to at least one of: a dental professional 1126, a health care provider 1124, an expert, an individual 1128, an e-commerce organization 1130, an artificial intelligence system 1106, a researcher, a manufacturer, a business, an application software, a patient portal, a system software, a client device, a processing device. Process a transaction of at least one of: an exchange, a transfer, a buy, a sell with at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, real time correlation dataset 1037 over a communication network, wherein a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform and provide to at least one of: a dental professional 1126, a health care professional 1124, an expert, an individual 1128, an e-commerce organization 1130, a researcher, a manufacturer, a business, an application software, a patient portal, a system software, a client device, a processing device.

The processing device 214 may execute the processing service 216 to provide to at least one of: a dental professional 1126, a health care professional 1124, an expert, an individual 1128, an e-commerce organization 1130, an artificial intelligence system, a researcher, a manufacturer, a business, an application software, a patient portal, a system software, a client device, processing device upon a process to: verify a compliance of at least one of: an individual 1128, an individual information dataset 1036 with a regulatory policy. Verify an authorization by an individual 1128 to analyze at least one of: a dental image 1002, a dental image landmark 1016, a real time correlation dataset. Authenticate an individual 1128 to process a transaction of at least one of: an exchange, a transfer, a buy, a sell of a dataset for at least one of: a currency, a data, a discount, a product, a good, a software, an application, an advertisement.

A processing device 214 may process information to and from an e-commerce organization 1130 that may include a dental insurance service. Wherein, a dental insurance service provides an insurance dataset. A dental insurance service may also include an insurance company or a claims data warehouse. A dental image 1002, a dental image landmark 1016 or a dataset may be provided by a dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device. Wherein, an e-commerce organization 1130 includes a dental insurance service, and wherein a dental insurance service provides an insurance dataset including at least one of: an American dental association (ADA) code, a date, a claim identifier, a claim number, a duplicate claim associated with the claim identifier, a provider national identification number, a provider's state license number, a provider identification number may be correlated to an insurance dataset and merged to at least one of: an artificial intelligence system, an artificial intelligence dataset, an artificial intelligence model. The insurance dataset may also be correlated to least one of: a dental image 1002, a dental image landmark 1016, an individual information dataset 1036 and provided to a real time correlation dataset 1037.

A processing device 214 may process information for a bioinformatics service. A bioinformatics service may be a genetic testing service or a geneotyping service. The bioinformatics service may be provided by a bioinformatics organization (such as a personal genomic or a research organization). A dental professional 1126, a health care professional 1124, an expert, an individual 1128, an e-commerce organization 1130, an artificial intelligence system, a researcher, a manufacturer, a business, an application software, a patient portal, a system software, a client device, a processing device may correlate at least one of: a dental image 1002, a dental image landmark 1016, a dataset to a bioinformatics dataset. An e-commerce organization 1130 includes a bioinformatics service, and wherein the bioinformatics service provides a bioinformatics dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, a diabetes diagnosis to further analyze and integrate the bioinformatics dataset and merge to at least one of: an artificial intelligence system 1106, an artificial intelligence dataset, an artificial intelligence model. The bioinformatics dataset may be correlated to least one of: a dental image 1002, a dental image landmark 1016, an individual information dataset 1036 and provided to a real time correlation dataset 1037.

A dental professional 1126, a health care professional 1124, an expert, an individual 1128, an e-commerce organization 1130, an artificial intelligence system 1106, a researcher, a manufacturer, a business, an application software, a patient portal, a system software, a client device, a processing device may use at least one of: supervised learning, unsupervised learning, an artificial intelligence system 1106 to process a transaction of least one: an exchange, a transfer, a buy, a sell of at least one of: a dental image 1002, a dental image landmark 1016, a supervised annotated dental anatomy landmark dataset 1003, an unsupervised annotated dental anatomy landmark dataset 1004, a supervised annotated dental pathology landmark dataset 1007, an unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product, an individual information dataset 1036, a biometric dataset 1040, a real time correlation dataset 1037 over a communication network, wherein a communication network includes at least one of: the internet, an intranet, an extranet, an internet, an internet transaction service, an online transaction service, a mobile network, a wireless network, a cloud platform, an online transaction processing (OLTP) service, an online analytical processing (OLAP) service, a transaction platform.

At least one of: a first artificial intelligence system, a second artificial intelligence system, a team of artificial intelligence systems may work individually or as a team in any order or combination. Further, at least one of: an artificial intelligence system, an artificial intelligence dataset, an artificial intelligence model does not necessarily imply sentient intelligence but may act as an interface of human interpretation rules and training that are provided to a single artificial intelligence or a team of artificial intelligence. Further, an artificial intelligence system, an artificial intelligence dataset, an artificial intelligence model may be based on human interpretation rules and training.

Figure 12:
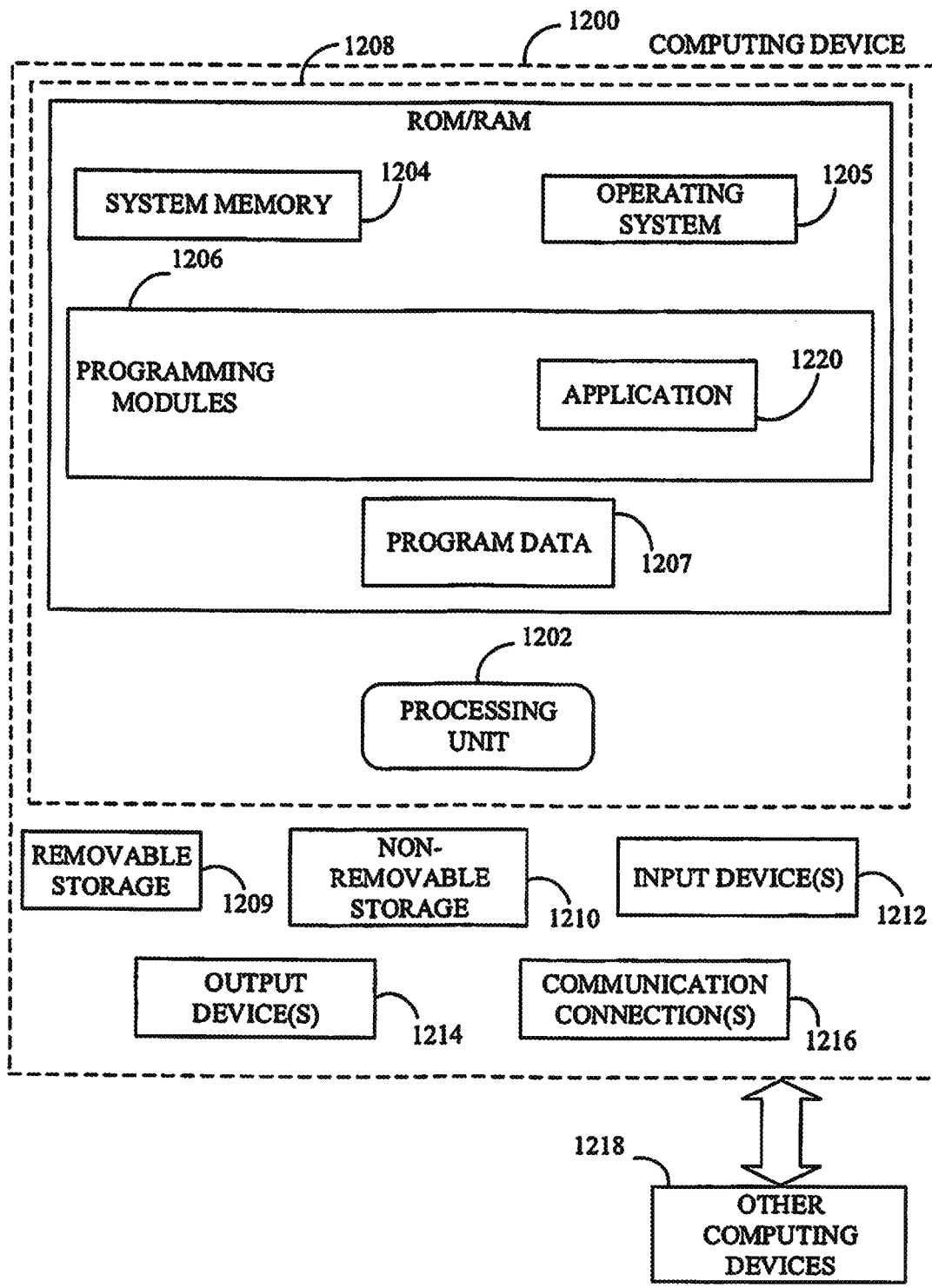
FIG. 12 is a block diagram of a computing device for implementing the methods disclosed herein, in accordance with some embodiments.

FIG. 12 is a block diagram of a system consistent with an embodiment of the disclosure that may include a computing device and/or cloud service, such as a computing device 1200. In a basic configuration, computing device 1200 may include at least one processing unit 1202 and a system memory 1204. Depending on the configuration and type of computing device, system memory 1204 may comprise, but is not limited to, volatile (e.g., random-access memory (RAM)), non-volatile (e.g., read-only memory (ROM)), flash memory, or any combination. System memory 1204 may include operating system 1205, one or more programming modules 1206, and may include a program data 1207. Operating system 1205, for example, may be suitable for controlling computing device 1200's operation. In one embodiment, programming modules 1206 may include image-processing module and/or a machine learning module. Embodiments of the disclosure may be practiced in conjunction with a graphics library, other operating systems, or any other application program and is not limited to any particular application or system. This basic configuration is illustrated in FIG. 12 by those components within a dashed line 1208.

Computing device 1200 may have additional features or functionality. For example, computing device 1200 may also include additional data storage devices (removable and/or non-removable) such as, for example, magnetic disks, optical disks, or tape. Such additional storage is illustrated in FIG. 12 by a removable storage 1209 and a non-removable storage 1210. Computer storage media may include volatile and non-volatile, removable and non-removable media implemented in any method or technology for storage of information, such as computer-readable instructions, data structures, program modules, or other data. System memory 1204, removable storage 1209, and non-removable storage 1210 are all computer storage media examples (i.e., memory storage). Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1200. Any such computer storage media may be part of device 1200. Computing device 1200 may also have input device(s) 1212 such as a keyboard, a mouse, a pen, a sound input device, a touch input device, a location sensor, a camera, a biometric sensor and/or a an electronic sensor 116. Output device(s) 1214 such as a display, speakers, a printer may also be included. The aforementioned devices are examples and others may be used.

Computing device 1200 may also contain a communication connection 1216 that may allow device 1200 to communicate with other computing devices 1218, such as over a network in a distributed computing environment, for example, an intranet or the internet. Communication connection 1216 is one example of communication media. Communication media may typically be embodied by computer-readable instructions, data structures, program modules, or other data in a modulated data signal, such as a carrier wave or other transport mechanism and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 1204, including operating system 1205. While executing on processing unit 1202, programming modules 1206 (e.g., application 1220 such as a media player) may perform processes including, for example, one or more stages of methods, algorithms, systems, applications, servers, databases as described above. The aforementioned process is an example, and processing unit 1202 may perform other processes.

Figure 13:
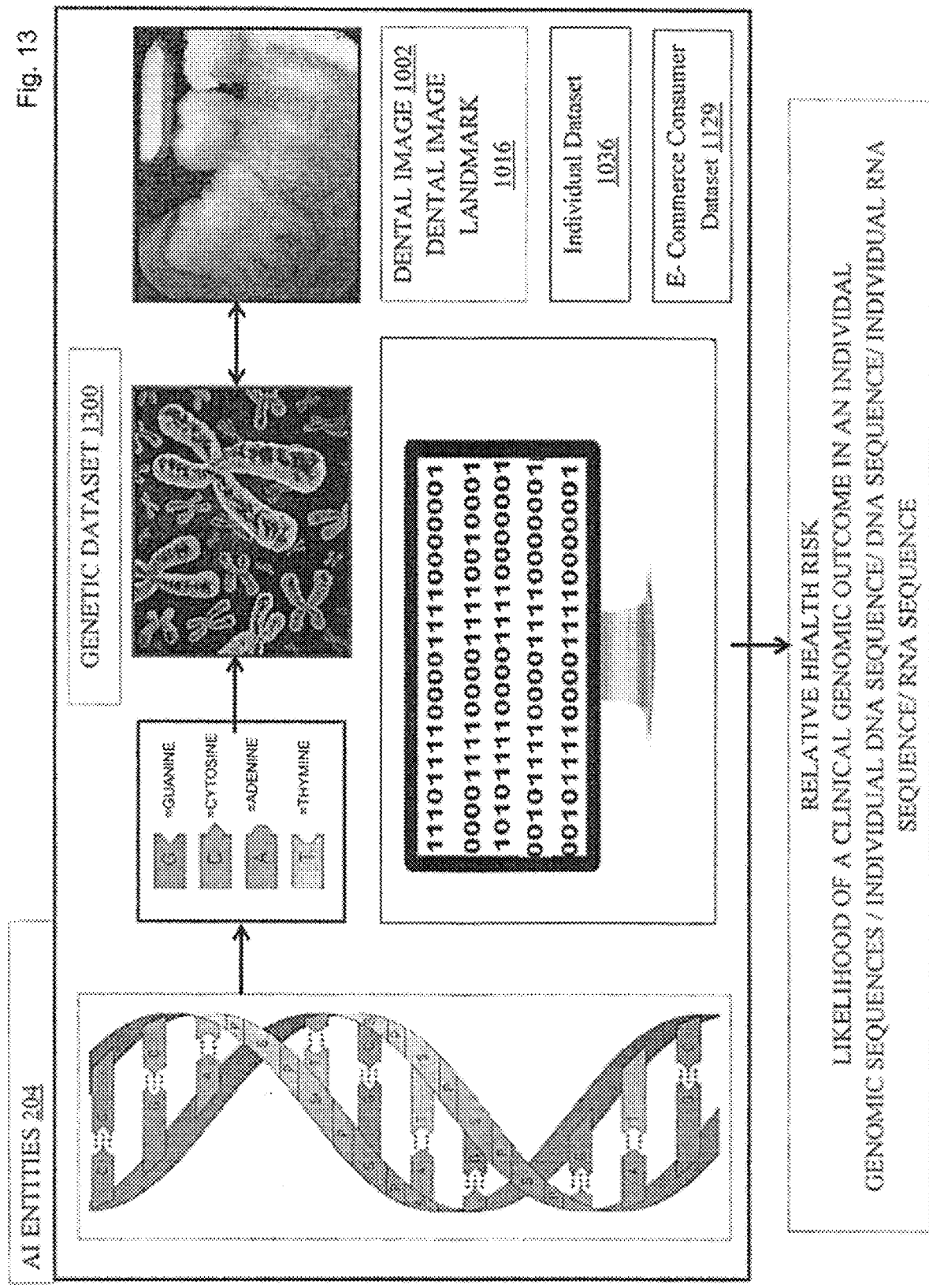
FIG. 13 is a conceptual diagram showing a genetic dataset being matched to a dental image via a processor to produce a at least one of: relative health risk, a likelihood of a clinical genomic outcome in an individual, a genomic sequence, an individual DNA sequence, an individual, RNA sequence, an RNA sequence.

FIG. 13 is a conceptual diagram demonstrating the Artificial Intelligence Entities 204 processing at least one of; a dental image 1002, a dental image landmark 1016, a genetic dataset 1300, an individual dataset 1036, an E-commerce consumer dataset 1129. The process will generate at least one of; a relative health risk, the likelihood of a genetic outcome in an individual, a genomic sequence, a DNA sequence, an individual DNA sequence, a RNA sequence, an individual RNA sequence.

Figure 14:
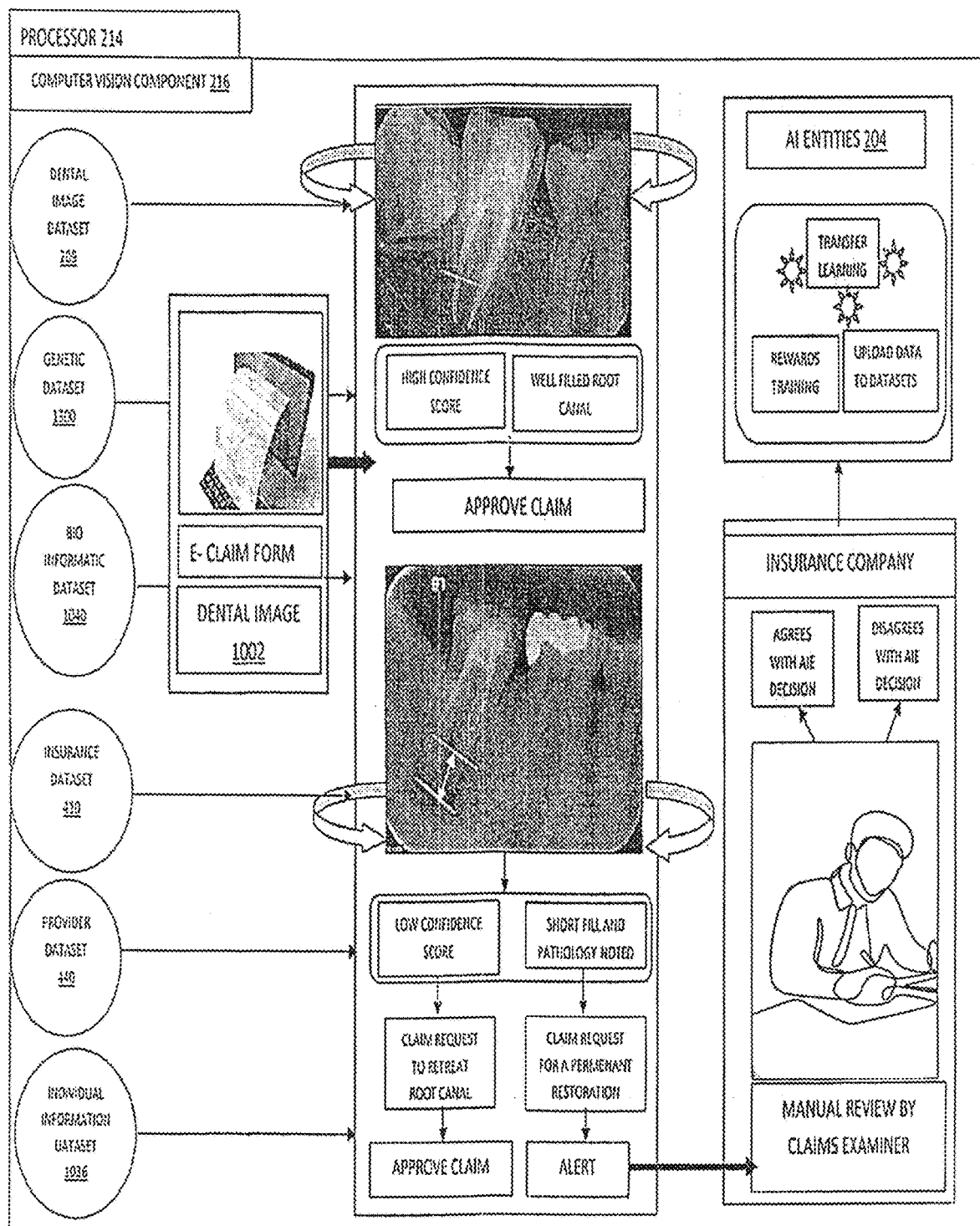
FIG. 14 is a conceptual diagram showing a dataset being associated with an e-claim form and a dental image generate a confidence score for a claim approval or a claim alert which would then be forwarded for a manual review by a claims examiner.

FIG. 14 is a conceptual diagram. A processor 214 may provide at least one of; an insurance claim form, a dental image 1002 to one or more artificial intelligence entities for analysis. The data may be formatted and any discrepancies corrected. The artificial intelligence entity may correlate the data with at least one of; a dental image dataset 209, a genetic dataset 1300, a bioinformatics dataset 1040, an insurance dataset 410, a provider dataset 440, a individual information dataset 1036. The images will be analyzed and compared to at least one of; a supervised annotated dental anatomy dataset 1003, an unsupervised annotated dental anatomy dataset 1004, a supervised annotated dental pathology dataset 1007, an unsupervised annotated dental pathology dataset 1008. The processor will utilize computer vision to process the image. The system will annotate the image noting the tooth numbers, any existing dental work, any pathology, and any deficits in the existing dental work. The system will query the insurance claim request. Upon verifying the correct image and tooth number (s) were provided the artificial intelligence entity will analyze the procedure being pre-approved. The artificial intelligence entity 204 will generate at least one of; a first treatment confidence score, a second treatment confidence score, a multiple treatment confidence score confidence score for the proposed treatment plan. These results may be polled and a final determination made by the polling results. A treatment plan with a high confidence score will receive an automatic approval and bypass the insurance examiner. In the figure the first image has what was determined to be a well filled root canal which generated a high confidence score for a permanent restoration. In the second image although the system detects a short fill and periapical pathology, it does not automatically reject the claim. In this case, the request to retreat the root canal generates a high confidence rating and the pre-authorization is automatically approved. A treatment request accompanied by an image that result in a low treatment confidence score will trigger an alert and the claim may be flagged for manual review by a claims examiner. The examiner may agree or disagree with the artificial intelligence entity decision. The measure of approval by the insurance examiner and insurance company will be uploaded via a communication network to the artificial intelligence entity for the purpose of rewards training and transfer learning. Thus, enabling the artificial intelligence component to make more accurate and faster decisions.

Figure 15:
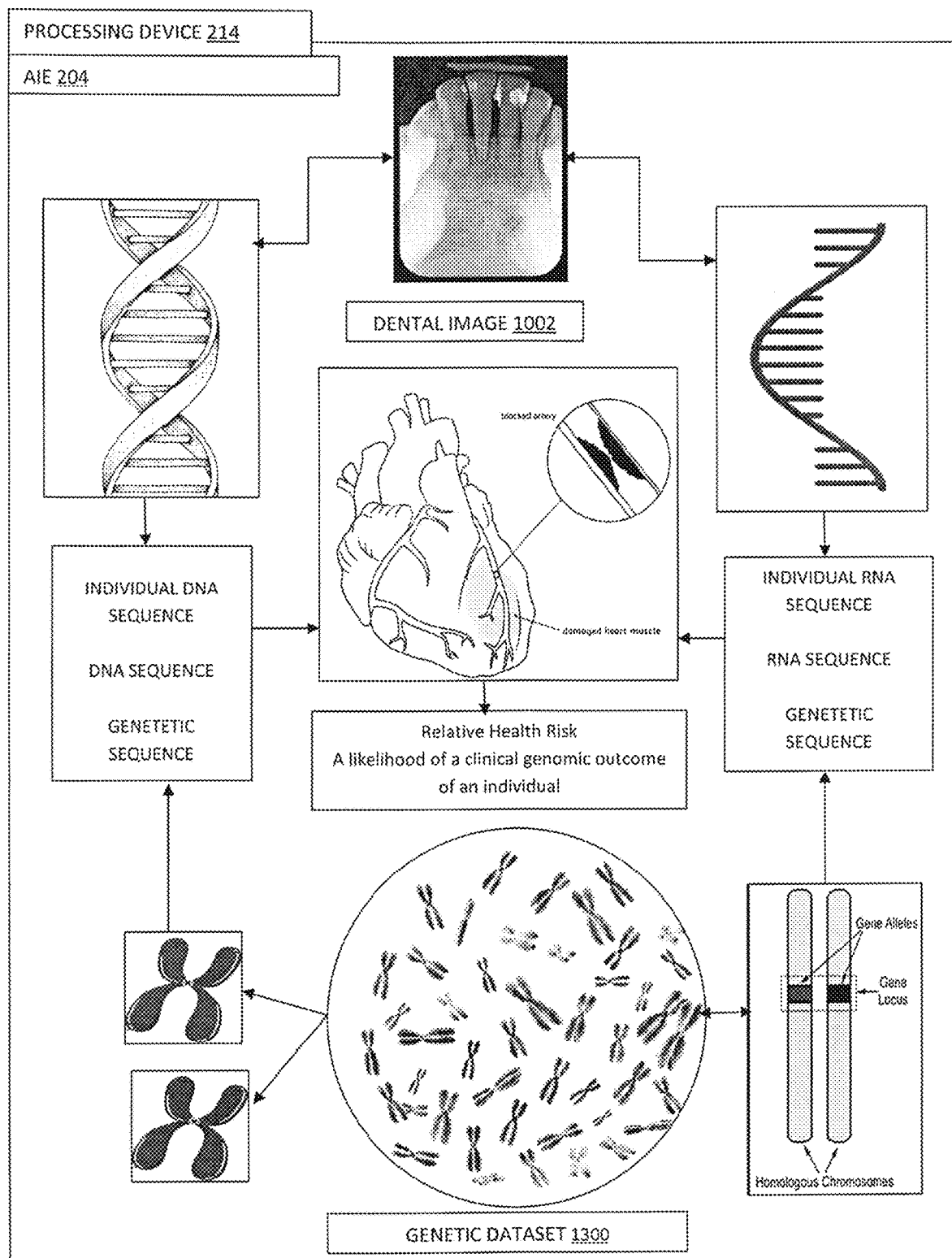
FIG. 15 is a conceptual diagram of a dental image being matched to at least one of: an individual DNA sequence, a DNA sequence, a genetic sequence, an individual RNA sequence, an RNA sequence, a genetic sequence to produce a relative health risk.

FIG. 15 is a conceptual diagram. A processor may analyze a dental image 1002 and utilize artificial intelligence entities to correlate the dental image 1002 to at least one of; a genetic dataset 1300, an individual RNA sequence, a RNA sequence, an individual DNA sequence, a DNA sequence. The system will generate at least one of; a relative health risk, a likelihood of genetic outcome, no health risk, no outlook of genetic outcome.

In another example scenario, a machine learning entity may include a bioinformatics machine learning service. A bioinformatics service may be at least one of: a genetic testing service, a geneotyping service. The bioinformatics machine learning service may be provided by a bioinformatics organization (such as a personal genomic or research organization). The microprocessor may correlate at least one of: a dental image, a dental image landmark, an image, an image landmark with a genetic dataset to generate a genetic connection. A genetic dataset may include at least one of: a node, genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, a medical condition. Further at least one of: a processing device, a processor, microprocessor may determining at least one of: a weight associated genetic connection between two directly connected nodes, the shortest genetic connection path, a weight associated with each genetic connection between two directly connected nodes and provide to at least one of: an e-commerce provider, an e-commerce consumer, an e-commerce administrator, a machine learning entity, an e-commerce organization, a person of interest a national security organization, a judiciary agency, a military agency, a government agency, a government, a law enforcement agency.

In another example scenario, a machine learning entity may include a bioinformatics machine learning service. A bioinformatics service may be at least one of: a genetic testing service, a geneotyping service. The bioinformatics machine learning service may be provided by a bioinformatics organization (such as a personal genomic or research organization). An aggregator may correlate dental image, the e-commerce dataset and the correlation dataset (which includes annotations) with a bioinformatics dataset. As such, the correlated dental images for at least one of: an e-commerce consumer, a person of interest may include attributes of an e-commerce dataset (such as the dental images for e-commerce and the annotations) that are further annotated with elements of the bioinformatics dataset. The correlated dental images for e-commerce dataset may also be merged into the bioinformatics dataset to expand the bioinformatics dataset for a future analysis.

The microprocessor may correlate at least one of: a dental image, a dental image landmark, an image, an image landmark with a genetic dataset to generate a genetic connection. A genetic dataset may include at least one of: a node, genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, a medical condition. Further, the microprocessor may determining at least one of: a weight associated genetic connection between two directly connected nodes, the shortest genetic connection path, a weight associated with each genetic connection between two directly connected nodes and provide to at least one of: an e-commerce provider, an e-commerce consumer, an e-commerce administrator, a machine learning entity, an e-commerce organization.

An aggregator may also identify whether at least one of: an e-commerce consumer, is informed in regards to a notification obligation such as at least one of: a HIPAA, an EULA, a SLA, a security token, a swipe authorization, a signed consent form by analyzing the e-commerce dataset for attributes associated with the notification obligation.

An aggregator may also identify matching elements of the bioinformatics dataset including gene(s) to at least one of: a node, a gene identifier, a gene sequence, single nucleotide polymorphism(s), nucleic acid sequence(s), protein sequence(s) (proteomics), an annotating genome(s), a shotgun sequence, an associated periodontal disease, a caries susceptibility, a malocclusion, a pathology, a medical condition, an impacted tooth, a tooth loss, a missing tooth, congenitally missing tooth, an angle's classification of malocclusion, level(s) of immunoglobulin G (IGG) and immunoglobulin A (IGA), diabetes diagnosis, among others by matching the attributes of the correlated dental images of the e-commerce dataset with elements of the bioinformatics dataset. The attributes of the correlated dental images for e-commerce dataset may further be annotated with the elements matched from the bioinformatics dataset.

At least one of: a microprocessor, an aggregator, a processor is configured to match and identify the likelihood of a clinical outcome of: at least one of an e-commerce consumer, a person of interest with a dental pathology comprising determination of a level of one or more of: a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset or an expression product thereof, in a biological sample obtained from at least one of: an e-commerce consumer, a person of interest. The method comprises assigning the one or more of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset or an expression product thereof, to one or more gene groups selected from a cellular organization gene group, basal epithelia gene group, a stress response gene group, an androgen gene group, a stromal response gene group, and a proliferation gene group. The method further comprises calculating a quantitative score for the patient by weighting the level of the one or more of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, an expression product to at least one of: a dental image, a dental image landmark, an image, an image landmark to predict the likelihood of a clinical genomic outcome for the patient based on the quantitative score. In an embodiment of the invention, an increase in the quantitative score correlates with an increased likelihood of a negative clinical pathology.

The microprocessor, which may also be a processor, may be configured to match and identify a dental pathology based on a genetic sample to at least one of: a dental image, an e-commerce dataset. Further the microprocessor may match and identify a genetic probability based on at least one of: a dental image, an e-commerce dataset. The microprocessor may further be configured to quantitatively determine a score by weighting a level from at least one of: a tissue sample, a deoxyribonucleic acid (DNA) sequence, a ribonucleic acid (RNA) sequence, a ribonucleic acid (RNA) transcripts sequence, a genetic sequence, an expression product in a biological sample and at least one of: associate, correlate it to at least one of: a dental image, a dental image landmark, an image, an image landmark predicting likelihood of clinical genomic outcome and provide to a bioinformatics dataset. The microprocessor may also compare a normalize level of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset of at least one reference gene to produce a normalized genomic expression levels and correlate it to at least one of: a dental image, an e-commerce consumer dataset. The microprocessor may compare a normalized genomic expression level of a gene to a range of normalize genomic expression levels of the same gene obtained from a dental pathology reference set and at least one of: associate, correlate it to at least one of: a dental image, an e-commerce dataset. Further, the microprocessor may be configured to predict a risk of dental pathology of at least one of: an e-commerce consumer, a person of interest based on the comparison of a normalized genomic expression levels of a gene to a normalized genomic expression levels of a gene and at least one of: associate, correlate it to at least one of: a dental image, an e-commerce dataset and provide to at least one of: an e-commerce provider, an e-commerce consumer, an e-commerce administrator, a machine learning entity, an e-commerce organization, a person of interest, a national security organization, a judiciary agency, a military agency, a government agency, a government, a law enforcement agency, a processor, a processing device.

At least one of: a microprocessor, an aggregator, a processor, a processing device is configured for contact tracing at least one of: an e-commerce consumer, a person of interest with an infection status and may be further configured for a contact tracing location. The process may be used for the identification of at least one of: an e-commerce consumer, a person of interest who may have come into contact with at least one of: an infected person, a non infected person and subsequent collection of further information about these contacts. By tracing the contacts of at least one of: an e-commerce consumer, a person of interest with an infected at least one of: an e-commerce consumer, a person of interest and testing them for infection and tracing their global contacts may provide valuable public health safety data. The public health aim may be to reduce infections in the population via this data. Diseases for which contact tracing are commonly performed include tuberculosis, measles, sexually transmitted infections, human immunodeficiency virus (HIV), Herpes simplex virus 1 and 2 (HSV-1 and HSV-2), blood-borne infections, ebola, bacterial infections, viral infections, parasitic infections, SARS, influenza, Covid-19, among others. The process will at least one of: associate, correlate at least one of: a dental image, an e-commerce consumer dataset of at one of: an e-commerce consumer, a person of interest with a bioinformatics dataset that may include a disease status and provide over a communication network to at least one of: an insurance company, a business, an e-commerce provider, an e-commerce consumer, an e-commerce administrator, a machine learning entity, an e-commerce organization, a national security organization, a judiciary agency, a military agency, a government agency, a government, a law enforcement agency, microprocessor, an aggregator, a processor, a processing device. Further at least one of: an association, a correlation of at least one of: a dental image, an e-commerce consumer dataset of at least one of: an e-commerce consumer, a person of interest with a bioinformatics dataset that may include at least one of: an infection status, a disease status, a contact tracing location and may be correlated to at least one of: a geographic location, a Global Position System (GPS), a Global Navigation System (GLONASS) and may be provide over a communication network to at least one of: an insurance company, a business, an e-commerce provider, an e-commerce consumer, an e-commerce administrator, a machine learning entity, an e-commerce organization, a national security organization, a judiciary agency, a military agency, a government agency, a government, a law enforcement agency, microprocessor, an aggregator, a processor, a processing device At least one of: a microprocessor, an aggregator, a processor is configured to match and identify the likelihood of a clinical outcome of: at least one of an e-commerce consumer, a person of interest with a dental pathology comprising determination of a level of one or more of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset or an expression product thereof, in a biological sample obtained from at least one of: an e-commerce consumer, a person of interest. The method comprises assigning the one or more of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset or an expression product thereof, to one or more gene groups selected from a cellular organization gene group, basal epithelia gene group, a stress response gene group, an androgen gene group, a stromal response gene group, and a proliferation gene group. The method further comprises calculating a quantitative score for the patient by weighting the level of the one or more of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset or an expression product to at least one of: the dental image, the dental image landmark, the image, and the image landmark to calculate a clinical outcome and predict the likelihood of a clinical genomic outcome for the patient based on the quantitative score. In another embodiment of the invention, a decrease in the quantitative score correlates with an increased likelihood of a negative clinical pathology.

The microprocessor, which may also be a processor, may be configured to match and identify a dental pathology based on a genetic sample to at least one of: a dental image, an e-commerce dataset. Further the microprocessor may match and identify a genetic probability based on at least one of: a dental image 108, an e-commerce dataset. The microprocessor may further be configured to match a dental image to a level of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset of a gene, that may be quantitatively determined, from at least one of: a tissue, a saliva sample, a sample obtained from at least one of: an e-commerce consumer, a person of interest and at least one of: associate, correlate it to at least one of: a dental image, an e-commerce consumer dataset. The microprocessor may also compare a normalize level of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset of a gene to levels of a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset of at least one reference gene to produce a normalized At least one of: a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset expression levels and correlate it to at least one of: a dental image, an e-commerce consumer dataset. The microprocessor may compare a normalized genomic expression level of a gene to a range of normalized genomic expression levels of the same gene obtained from a dental pathology reference set and at least one of: associate, correlate it to at least one of: a dental image, an e-commerce dataset. Further, the microprocessor may be configured to predict a risk of dental pathology of at least one of: an e-commerce consumer, a person of interest based on the comparison of a normalized genomic sequence expression levels of a gene to a normalized genomic sequence expression levels of a gene and at least one of:

associate, correlate it to at least one of: a dental image, an e-commerce dataset and provide to at least one of: an e-commerce provider, an e-commerce consumer, an e-commerce administrator, a machine learning entity, an e-commerce organization, a person of interest, a national security organization, a judiciary agency, a military agency, a government agency, a government, a law enforcement agency, a processor, a processing device.

A system of identifying a relative genomic health risk from at least one of: a dental image, a dental image landmark, an image, an image landmark to at least one of: a deoxyribonucleic acid (DNA) sequence, a ribonucleic acid (RNA), a genomic sequence associated with an individual information dataset, the system comprising a processor, wherein the processor configured to receive at least one of: a dental image, a dental image landmark, an image, an image landmark. Wherein, the processor may be configured to execute an instruction in any order. Wherein, the processor device may be configured to omit an instruction in any order. Wherein an instruction is at least one of: a match, an identify, a score, a rule, a train, a process, an exchange, a transfer, a purchase, a sell. Wherein at least one of: a deoxyribonucleic acid (DNA) sequence, a ribonucleic acid (RNA), a sequence genomic sequence contains at least one nucleotide. Match at least one of: a dental image, a dental image landmark, an image, an image landmark and a quantitative score by weighting level of at least one of: an deoxyribonucleic acid (DNA) sequence, a ribonucleic acid (RNA), a sequence, a genomic sequence of an individual to identify a relative genomic health risk and provide to a dental image dataset. Determine an image variant in at least one of: a dental image, a dental image landmark, an image, an image landmark and match it with at least one of: an deoxyribonucleic acid (DNA) sequence, a ribonucleic acid (RNA) sequence, a genomic sequence to determine a relative genomic health risk and provide to a real time dental image dataset. Determine if no image variant is detected in at least one of: a dental image, a dental image landmark, an image, an image landmark and match it with at least one of: an deoxyribonucleic acid (DNA), sequence, a ribonucleic acid (RNA), sequence, a genomic to determine a relative genomic health risk and provide to a real time dental image dataset. Match and identify a real time dental image dataset to an individual information dataset and provide to a real time correlation dataset; the processor may be configured to generate at least one of: a dental product recommendation, a product recommendation, a dental treatment recommendation, a treatment recommendation, a relative health risk and provide to a to a real time correlation dataset.

Process a transaction of at least one of: an exchange, a transfer, a purchase, a sell of at least one of: a dental image, a dental image landmark, an image, an image landmark, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, a real time dental image dataset, an individual information dataset, a dental product recommendation, a product recommendation, a dental treatment recommendation, a treatment recommendation, a relative health risk, a real time correlation dataset, a data over a communication network; wherein a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform.

Another aspect is a method of identifying a genetic probability from matching and identifying at least one of: a genetic sample, a genetic sequence to at least one of: a dental image, a dental image landmark, an image, an image landmark wherein the method comprising: a microprocessor configured to match and identify at least one of: a genetic probability, a relative health risk based on at least one of: a dental image, a dental image landmark, an image, an image landmark and provide to a dental image dataset. The processor may be configured to execute an instruction in any order; the processor device may be configured to omit an instruction in any order; wherein an instruction is at least one of: a quantitatively, a normalize, a comparing, a predict, a match, an identify, a process, an exchange, a transfer, a purchase, a sell; quantitatively determining a score by weighting a level of at least of: a deoxyribonucleic acid (DNA) sequence, an individual deoxyribonucleic acid (DNA) sequence, a ribonucleic acid (RNA) sequence, an individual ribonucleic acid (RNA) sequence, a RNA transcript sequence of a gene, a genetic sequence and at least one of: associate, correlate it to at least one of: a dental image, a dental image landmark, an image, an image landmark and provide to dental image dataset;

normalize a level of a deoxyribonucleic acid (DNA) sequence, an individual deoxyribonucleic acid (DNA) sequence, a ribonucleic acid (RNA) sequence, an individual ribonucleic acid (RNA) sequence, a RNA transcript sequence of a gene, a genetic sequence of a gene to at least one reference gene to produce a normalized gene expression level and at least one of: associate, correlate it to at least one of: a dental image, a dental image landmark, an image, an image landmark and provide to a dental image dataset.

Comparing a normalized gene expression level of a gene to a range of normalized gene expression levels of a reference gene obtained from at least one of: a dental anatomy dataset reference dataset, a dental pathology reference dataset, a reference dataset set and at least one of: associate, correlate it to at least one of: a dental image, a dental image landmark, an image, an image landmark and provide to a dental image dataset. Predict a relative health risk of at least one of: a pathology, a dental pathology, no pathology based on the comparison of a normalized level of at least one of: a deoxyribonucleic acid (DNA) sequence, an individual deoxyribonucleic acid (DNA) sequence, a ribonucleic acid (RNA) sequence, an individual ribonucleic acid (RNA) sequence, a RNA transcript sequence of a gene, a genetic sequence expression level of a gene to a normalized reference gene dataset and at least one of: associate, correlate it to at least one of: a dental image, a dental image landmark, an image, an image landmark and provide to a dental image dataset. Match and identify a dental image dataset to an individual information dataset to produce a real time correlation dataset.

At least one of: a processor, a microprocessor, an aggregate server may be configured to generate at least one of: a dental product recommendation, a product recommendation, a dental treatment recommendation, a treatment recommendation, a relative health risk and provide to a to a real time correlation dataset. Process a transaction of at least one of: an exchange, a transfer, a purchase, a sell of at least one of: a dental image, a dental image landmark, an image, an image landmark, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, dental image dataset, an individual information dataset, a dental product recommendation, a product recommendation, a dental treatment recommendation, a treatment recommendation, a relative health risk, a real time correlation dataset, a data over a communication network; wherein a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform.

Another method of generating at least one of: a dental treatment recommendation, a treatment recommendation, a dental product recommendation, a product recommendation, a relative health risk based on image processing comprising a processor configured to receive, using at least one of: a processing device, a communication device at least one patient data from at least one of: a dental professional, a health care professional, an expert, an e-commerce consumer, an individual, an e-commerce organization, a business, an artificial intelligence system, a researcher, a manufacturer, an application software, a patient portal, a system software, a client device, a processing device, an insurance company, a bioinformatics organization comprising at least one image from at least one of: an expert device, a processing device, a patient device. Retrieve, using a storage device at least one dental dataset. Analyze, using a processing device, at least one patient data and at least one dental dataset, wherein at least one dental dataset is associated with at least one patient data, wherein at least one dental dataset comprises at least one of: a classified dental image anatomy dataset, a classified dental image pathology dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset. Generate, using a processing device, at least one landmark based on analyzing, wherein at least one landmark comprises at least one dental characteristic associated with at least one patient data. Retrieve, using a storage device, at least one dental reference dataset. Process, using a processing device, at least one landmark and at least one dental reference dataset and determine, using a processing device, at least one of: a dental treatment recommendation, a treatment recommendation, a dental product recommendation, a product recommendation, a relative health risk based on a processing. Transmit, using at least one of: a processing device, a communication device at least one of: a dental treatment recommendation, a treatment recommendation, a dental product recommendation, a product recommendation, a relative health risk. Transmit, using at least one of: a processing device, a communication device at least one of: a dental treatment recommendation, a treatment recommendation, a dental product recommendation, a product recommendation, a relative health risk and at least one patient data to at least one of: an expert device, a processing device, a patient device associated with at least one expert and store, using a storage device, at least one of: a dental treatment recommendation, a treatment recommendation, a dental product recommendation, a product recommendation, a relative health risk. Receive, using at least one of: a processing device, a communication device a first confidence score from at least one of: an expert device, a processing device, a patient device, wherein a first confidence score is associated with at least one of: a dental treatment recommendation, a treatment recommendation, a dental product recommendation, a product recommendation, a relative health risk. Receive, using at least one of: a processing device, a communication device at least one of: a second confidence score, a multiple confidence score from at least one of: an expert device, a processing device, a patient device. Wherein a second confidence score is associated with at least one landmark and wherein a multiple confidence score is associated with at least one landmark. Transmit, using at least one of: a processing device, a communication device a first confidence score to at least one external device. Then transmit, using at least one of: a processing device, a communication device at least one of: a second confidence score, a multiple confidence score to at least one external device. Update, using a processing device, at least one dental reference dataset with at least one patient data and at least one of: a dental treatment recommendation, a treatment recommendation, a dental product recommendation, a product recommendation, a relative health risk based on at least one of: a first confidence score, a second confidence score, a multiple confidence score. Generate, using a processing device, at least one updated reference dataset based on updating of at least one dental reference dataset and store, using a storage device, at least one updated reference dataset. Receive an order from at least one patient device, wherein an order is associated with at least one of: a dental treatment recommendation, a treatment recommendation, a dental product recommendation, a product recommendation, a relative health risk. Transmit, using at least one of: a processing device, a communication device an order to at least one external device. Receive, using at least one of: a processing device, a communication device a response corresponding to an order from at least one external device. Transmit, using at least one of: a processing device, a communication device a response to at least one patient device. Generate, using a processing device, a validity notification corresponding to at least one patient data based on an analyzing, wherein a validity notification is associated with a measure of approval of at least one patient data; transmit, using at least one of: a processing device, a communication device a validity notification to at least one external device. Retrieve, using a storage device, at least one regulatory data based on at least one first user. Analyze, using a processing device, at least one first user data based on at least one regulatory data. Generate, using a processing device, a notification corresponding to at least one first user based on an analyzing of at least one first user data. Transmit, using at least one of: a processing device, a communication device a notification to at least one of: at least one patient device, at least one external device;

process a transaction from at least one of: a dental professional, a health care professional, an expert, an e-commerce consumer, an individual, an e-commerce organization, a business, a researcher, a government agency, a manufacturer, a business, an application software, a system software, a client device, a processing device of at least one of: an exchange, a transfer, a purchase, a sell of a dataset. Wherein a dataset includes at least one of: one patient data, one dental dataset, one dental reference dataset, one landmark, one dental recommendation, a classified dental image anatomy dataset, a classified dental image pathology dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, a first confidence score, a second confidence score, a multiple confidence score, one dental product recommendation, a validity notification over at least one of: a processing device, a communication device, a communication network.

In another embodiment at least one of: a microprocessor, an aggregator, a processor, a processing device is configured to use at least one of: a deep learning mechanism, a machine learning mechanism to offer a third party financing company option when at least one of: an e-commerce consumer, a person of interest, a patient has at least one of: a treatment obstacle, a financial obstacle, an insurance obstacle, a payment obstacle. A storage device may be configured for retrieving details of at least one third party financing company and provide it to at least one of: a microprocessor, an aggregator, a processor, a processing device. Further, at least one of: a microprocessor, an aggregator, a processor, a processing device may be configured against economic discrimination of at least one of: a treatment obstacle, a financial obstacle, an insurance tier, an insurance payment and offer all option(s) to at least one of: an e-commerce consumer, a person of interest, a patient. Under some circumstances at least one of: a microprocessor, an aggregator, a processor, a processing device may be configured not to economically discrimination of at least one of: a treatment obstacle, a financial obstacle, an insurance tier, an insurance payment. A circumstance may be unemployment, bankruptcy, divorce, among other. Under common circumstances, offering all option(s) is considered the standard of care by most e-commerce providers.

Wherein at least one of: an e-commerce provider, a deep learning service, a machine learning service, an e-commerce organization includes at least one of: an insurance service, a dental insurance service. A dental insurance service may include at least one of: an insurance company, an insurance entity, a claims data warehouse. In an example scenario, the machine learning entity may include an insurance machine learning service. A dental insurance service may be an insurance company. At least one of: insurance machine learning service, a dental machine learning service may be provided by at least one of: a dental insurance, a medical insurance organization. At least one of: a microprocessor, a processor, an aggregator may correlate a dental image and an e-commerce consumer dataset and analyze with an insurance dataset. As such, the correlated dental images of at least one of: an e-commerce consumer, a person of interest may include attributes of the e-commerce dataset (such as the dental images for e-commerce and the annotations) that are further annotated with elements of the insurance dataset. An aggregator may also format the correlated dental images for an e-commerce provider with an insurance claim. In addition, an aggregator may integrate the correlated dental images of at least one of: an e-commerce consumer, a person of interest to a new or an existing insurance claim. The correlation dataset and an e-commerce dataset may also be analyzed and merged (or integrated) into the insurance dataset to expand the insurance dataset for a future analysis.

The microprocessor is further configured to receive a dental image and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance claim dataset. Further, the microprocessor may at least one of: match and identify an insurance dataset to a dental image, verify tooth numbers and provide to an insurance dataset, verify an insurance code and provide to an insurance dataset, alert a discrepancies in an insurance dataset and provide an insurance dataset to at least one of: an insurance company, a business, an e-commerce provider, an e-commerce consumer, an e-commerce administrator, a machine learning entity, an e-commerce organization, a national security organization, a judiciary agency, a military agency, a government agency, a government, a law enforcement agency, a processing device.

An aggregator may also identify discrepancy(s) between dental insurance claim(s) by analyzing and comparing attributes of the correlated dental images of at least one of: an e-commerce consumer, a person of interest and an e-commerce dataset with elements of the insurance dataset including at least one of: American Dental Association (ADA) code(s), an insurance code, a date, an insurance claim data, a claim identifier, a claim number, multiple or duplicate claims (instead of a single claim), a national provider identification number for provider/institution(s), a provider's state license number, a license, among others. Corrective action to merge the discrepancy(s) may be implemented automatically to remove the discrepancy(s) between the correlated dental images for at least one of: an e-commerce consumer, a person of interest, the e-commerce dataset, an insurance claim from the insurance dataset. Alternatively, corrective action may be implemented manually based on at least one of: feedback, input from at least one of: an e-commerce provider, an e-commerce consumer, an e-commerce administrator, a machine learning entity, an e-commerce organization, a government entity, a law enforcement entity, a person of interest associated with an aggregator regarding the discrepancy(s).

An example of processing a dataset with cluster analysis with at least one of: deep learning, machine learning for at least one of: an insurance service, dental insurance service. A dental insurance service and/or an insurance service may include at least one of: an insurance company, an insurance entity, a claims data warehouse.

A microprocessor may be configured to receive at least one of: a dental image dataset, an insurance dataset, a provider dataset, an e-commerce dataset and correlate to at least one of: a tooth number, an American Dental Association (ADA) code, an insurance code, a date, an insurance claim data, a claim identifier, a claim number, a duplicate claim associated with the claim identifier, a provider national identification number, a provider's state license number, a license, a provider identification number to an insurance claim dataset. The correlation of the dataset may occur with deep learning and/or machine learning. Another process may use a cluster analysis to produce a correlation dataset and provide to at least one of: an insurance company, a business, an e-commerce provider, an e-commerce consumer, an e-commerce administrator, a machine learning entity, an e-commerce organization, a national security organization, a judiciary agency, a military agency, a government agency, a government, a law enforcement agency, a microprocessor, a processing device, a processor.

Further, the microprocessor may at least one of: match and identify an insurance dataset to a dental image, verify tooth numbers and provide to an insurance dataset, verify an insurance code and provide to an insurance dataset, alert a discrepancies in an insurance dataset and provide an insurance dataset to at least one of: an insurance company, an insurance entity, a claims data warehouse, a business, an e-commerce provider, an e-commerce consumer, an e-commerce administrator, a machine learning entity, an e-commerce organization, a national security organization, a judiciary agency, a military agency, a government agency, a government, a law enforcement agency, a microprocessor, a aggregator, a processing device, a processor.

At least one of: a microprocessor, a processing device, an aggregator, a processor may also identify discrepancy(s)

between dental insurance claim(s) by analyzing and comparing attributes of the correlated dental images of an e-commerce consumer, a person of interest and an e-commerce dataset with elements of the insurance dataset including at least one of: American Dental Association (ADA) code(s), an insurance code, a date, an insurance claim data, a claim identifier, a claim number, multiple or duplicate claims (instead of a single claim), a national provider identification number for provider/institution(s), a provider's state license number, a license, among others. Corrective action to merge the discrepancy(s) may be implemented automatically to remove the discrepancy(s) between the correlated dental images for at least one of: an e-commerce consumer, a person of interest, the e-commerce dataset, an insurance claim from the insurance dataset. Alternatively, corrective action may be implemented manually based on at least one of: feedback, input from at least one of: an e-commerce provider, e-commerce consumer, e-commerce administrator, a machine learning entity, an e-commerce organization, a government entity, a law enforcement entity, a person of interest associated with at least one of: a processor, a microprocessor, an aggregator regarding the discrepancy(s).

An e-commerce consumer may retain at least one of: their dental images, their datasets on their client device that may include at least one of: a server, a dental office server, a network node, a desktop computer, a workstation, a laptop computer, a cell phone, a tablet, a mobile device, an augmented reality display, virtual reality display, among others. Further a client device may be configured against using devices such as a server, a dental office server, a network node, a desktop computer, a workstation, a laptop computer, a cell phone, a tablet, a mobile device, an augmented reality display, virtual reality display, among others.

A system may generating at least one of: an insurance claim approval, an insurance claim denial, an insurance claim for human review, by comparing images to attached to a claim with a dental image dataset, the system comprising a processer, wherein the processor configured to: receive an insurance claim with at least one insurance data and associated with at least one dental image. The system may execute an instruction in any order. The system may omit an instruction in any order. Wherein an instruction is at least one of: a match, an identify, a score, a rule, a train, a process, an exchange, a transfer, a purchase, a sell. Match and identify a dental image to a dental dataset and provide to a dental image dataset. Wherein a dental dataset comprises at least one of: a classified dental image anatomy dataset, a classified dental image pathology dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset. Wherein, a dental image contains at least one of: a dental image, a dental image landmark, an image, an image landmark, an image, an image landmark. Verify and correct a dental image with a dental dataset and provide to a dental image dataset. Verify and correct an insurance data with an insurance dataset and provide to a dental image dataset. Wherein an insurance dataset including at least one of: an American dental association (ADA) code, a date, a claim identifier, a claim number, a duplicate claim associated with the claim identifier, a provider national identification number, a provider's state license number, a provider identification number, a data. Further, correlate an insurance dataset to least one of: a dental image, a dental image landmark, an image, an image landmark, an image, an image landmark with an individual information dataset and provide to the real time correlation dataset. At least one of: a microprocessor, a processor, an aggregator may be configured to generate at least one of: an insurance claim approval, an insurance claim denial, a treatment recommendation, a product recommendation, a relative health risk and provide to the real time correlation dataset.

Process a transaction of at least one of: an exchange, a transfer, a purchase, a sell of at least one of: a dental image, a dental image landmark, an image, an image landmark, a classified dental image anatomy dataset, a classified dental image pathology dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, an individual information dataset, an insurance claim approval, an insurance claim denial, a treatment recommendation, a product recommendation, a relative health risk, a data over a communication network; wherein a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform.

A method of generating at least one of: an insurance recommendation, a dental recommendation, a recommendation, a relative health risk based on image processing. Wherein a method comprises a processor configured to receive, using at least one of: a processing device, a communication device at least one patient data from at least one of: a dental professional, a health care professional, an expert, an e-commerce organization, an individual, an e-commerce organization, a business, a researcher, a manufacturer, an application software, a patient portal, a system software, a client device, a processing device, an insurance company, a bioinformatics organization. Further, comprising at least one image from at least one of: an expert device, a processing device, a patient device that may retrieve, using a storage device, at least one dental dataset. Analyze, using a processing device, at least one patient data and at least one dental dataset, wherein at least one dental dataset is associated with at least one patient data. Wherein, at least one dental dataset comprises at least one of: a classified dental image anatomy dataset, a classified dental image pathology dataset, an insurance data, an insurance dataset, wherein an insurance dataset includes at least one insurance data.

Generate, using a processing device, at least one landmark based on analyzing, wherein at least one landmark comprises at least one dental characteristic associated with at least one patient data and retrieve, using a storage device, at least one dental reference dataset while process, using a processing device, at least one landmark and at least one dental reference dataset. Determine, using a processing device, at least one of: an insurance recommendation, a dental recommendation, a recommendation, a relative health risk based on a processing and transmit, using at least one of: a processing device, a communication device at least one of: an insurance recommendation, a dental recommendation, a recommendation, a relative health risk. Further, transmit, using at least one of: a processing device, a communication device at least one of: an insurance recommendation, a dental recommendation, a recommendation, a relative health risk and at least one patient data to at least one of: an expert device, a processing device, a patient device associated with at least one expert. Store, using a storage device, at least one of: an insurance recommendation, a dental recommendation, a recommendation, a relative health risk; receive, using at least one of: a processing device, a communication device a first confidence score from at least one of: an expert device, a processing device, a patient device, wherein a first confidence score is associated with at least one of: an insurance recommendation, a dental recommendation, a recommendation, a relative health risk. The processor may receive, using at least one of: a processing device, a communication device at least one of: a second confidence score, a multiple confidence score from at least one of: an expert device, a processing device, a patient device, wherein a second confidence score is associated with at least one landmark and wherein a multiple confidence score is associated with at least one landmark. Transmit, using at least one of: a processing device, a communication device a first confidence score to at least one external device. Transmit, using at least one of: a processing device, a communication device at least one of: a second confidence score, a multiple confidence score to at least one external device and update, using a processing device, at least one dental reference dataset with at least one patient data and at least one of: an insurance recommendation, a dental recommendation, a recommendation, a relative health risk based on at least one of: a first confidence score, a second confidence score, a multiple confidence score.

Generate, using a processing device, at least one updated reference dataset based on updating of at least one dental reference dataset and store, using a storage device, at least one updated reference dataset. Receive an order from at least one patient device, wherein an order is associated with at least one of: an insurance recommendation, a dental recommendation, a recommendation, a relative health risk. Transmit, using at least one of: a processing device, a communication device an order to at least one external device and receive, using at least one of: a processing device, a communication device a response corresponding to an order from at least one external device. Transmit, using at least one of: a processing device, a communication device a response to at least one patient device.

Generate, using a processing device, a validity notification corresponding to at least one patient data based on an analyzing, wherein a validity notification is associated with a measure of approval of at least one patient data and transmit, using at least one of: a processing device, a communication device a validity notification to at least one external device to retrieve, using a storage device, at least one regulatory data based on at least one first user. Analyze, using a processing device, at least one first user data based on at least one regulatory data; generate, using a processing device, a notification corresponding to at least one first user based on an analyzing of at least one first user data and transmit, using at least one of: a processing device, a communication device a notification to at least one of: at least one patient device, at least one external device.

Process a transaction from at least one of: a dental professional, a health care professional, an expert, an e-commerce consumer, an individual, an e-commerce organization, a business, a researcher, a government agency, a manufacturer, a business, an application software, a system software, a client device, a processing device of at least one of: an exchange, a transfer, a purchase, a sell of a dataset, wherein a dataset includes at least one of: one patient data, one dental dataset, one dental reference dataset, one landmark, one dental recommendation, a first confidence score, a second confidence score, a multiple confidence score, one dental product recommendation, an insurance recommendation, a relative health risk, a validity notification over at least one of: a processing device, a communication device, a communication network. Wherein at least one of: a processing device, a communication device, a communication network includes at least one of: the internet, an intranet, an extranet, an internet, an internet transaction service, an online transaction service, a mobile network, a cell phone, a wearable technology, a wireless network, a cloud platform, an online transaction processing (OLTP) service, an online analytical processing (OLAP) service, a transaction platform and provide to at least one of: a dental professional, a health care professional, an expert, a processing device, a patient device, an individual, an e-commerce organization, a researcher, a business, a government agency, a manufacturer, a business, an application software, a system software, a client device, a processing device.

Format the real time dental image dataset based on a transaction processed by at least one of: a dental image, a dental image landmark, an image, an image landmark, a supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a bioinformatics dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, an, e-commerce consumer, an individual, an e-commerce organization, a business, a real time correlation dataset; merge the real time dental image dataset with a transaction processed at least one of: a dental image, a dental image landmark, an image, an image landmark, a supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a bioinformatics dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, an e-commerce consumer, an individual, an e-commerce organization, a business, a real time correlation dataset into the real time correlation dataset; and identify and correct a discrepancy between the real time dental image dataset with a transaction processed by the at least one of: a dental image, a dental image landmark, an image, an image landmark, a supervised annotated dental anatomy landmark dataset, an unsupervised annotated dental anatomy landmark dataset, a supervised annotated dental pathology landmark dataset, an unsupervised annotated dental pathology landmark dataset, a real time dental image dataset, a supervised annotated dental treatment recommendation dataset, an unsupervised annotated dental treatment recommendation dataset, a real time dental treatment recommendation dataset, a real time dental treatment recommendation, a real time dental treatment recommendation for no treatment, a supervised annotated dental product recommendation dataset, an unsupervised annotated dental product recommendation dataset, a real time dental product recommendation dataset, a real time dental product recommendation, a real time dental product recommendation for no product, an individual information dataset, a bioinformatics dataset, a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, an e-commerce consumer, an individual, an e-commerce organization, a business, a real time correlation dataset and the real time correlation dataset.

Dental images 1002 may be stored in a variety of formats and extensions and are proprietary to the manufactures of the dental image sensor. Format(s) and extension(s) may be considered interchangeable terms. Dexis stores it's dental images 1002 in a .dex format where Tigerview stores it's dental images 1002 in a .tig format. Cerec opted to store it's dental images 1002 in a .stl format whereas Schick opted to store it's dental images in a .sidexis format. Eagelsoft stores it's dental images 1002 in a .jtif format, Gendex/Kavo Orthopanagraph stores it's dental images 1002 in a .jpg2000 format, and Kodak stores it's dental images 1002 in a .rvg format. Additional formats and extensions may include .gif, .png, .bitmap, .dicom, .ios, .mri, .dcm, .raw. These are only an example of dental image and medical image formats and extensions and are not to be considered inclusive of all dental image and medical image formats and extensions. Although, each dental sensor manufacture has it's own proprietary format and extension many dental sensor manufactures allow export of their dental images 1002 in a .jpeg format.

Document extension, which may be used image datasets may include the following format(s) and/or extension(s): .doc, .html, .odt, .pdf, .xls, .xlsx, .odt, .ppt, .pptx, .txt, .sms, .mms, .docx, .docm, .dotx, .dptm, .dot, .xps, .mht, .mhtml, .htm, .rtf, .xml, .odt, .wps. Further, datasets and data files, which may be used for image datasets may include the following format(s) and/or extension(s): .dat, .xlsx, .xlsm, .xltx, .xltm, .sql, .db, .mdb, .accdb. These are only an examples of document extensions and formats are not to be considered inclusive of all document extension formats and extensions.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers. Embodiments of the disclosure may also be practiced in distributed computing environments where tasks are performed by remote processing devices that are linked through a communications network. In a distributed computing environment, program modules may be located in both local and remote memory storage devices.

Embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams, illustration diagrams and conceptual diagrams of methods, systems, and computer program products according to embodiments of the disclosure. The functions/acts noted in the blocks may occur out of the order as shown in any flowchart. For example, two blocks shown in succession may, in fact, be executed substantially concurrently or the blocks may sometimes be executed in the reverse order, depending upon the functionality/acts involved. Further, at least one of: a processing device, processing service, aggregator server, a communication device is configured to at least one of: execute an instruction in any order, omit an instruction in any order. Wherein an instruction may include one of: a match, an identify, a score, a rule, a train, a process, an exchange, a transfer, a purchase, a sell, a receive, a retrieve, a transmit, an analyze, a generate, a transmit, an order.

While certain embodiments of the disclosure have been described, other embodiments may exist. Although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the internet, or other forms of RAM or ROM. The disclosed method's stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

The invention claimed is:

1. A method of implemented on a processing device for generating at least one of: a dental product recommendation, a product recommendation, a dental treatment recommendation, a treatment recommendation, a relative health risk based on at least one of: a dental image, a dental image landmark, an image, an image landmark, an image landmark matched to at least one of: a deoxyribonucleic acid (DNA) sequence, an individual deoxyribonudeic acid (DNA) sequence, a ribonucleic acid (RNA) sequence, an individual ribonucleic acid (RNA) sequence, a genetic sequence, and a dataset; the method comprising using a processing device, wherein the method implemented on the processing device is configured to: receive at least one of
    the dental image, the dental image landmark, the image, the image landmark, and the image landmark from at least one of:
    a dental professional, a health care professional, an expert, an e-commerce consumer, an individual, an e-commerce organization, a business, an artificial intelligence system, a researcher, a manufacturer, an application software, a patient portal, a system software, a client device, an insurance company, a bioinformatics organization and the processing device;
    wherein the method implemented on the processing device may execute an instruction in any order;
        train the processing device to use machine learning, to calculate a quantitative score by weighting the level of at least one of: a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, a dataset, and an expression product and
        at least one of: the dental image, the dental image landmark, the image, the image landmark, and the image landmark
        to produce at least one of: the dental treatment recommendation, the treatment recommendation, the dental product recommendation, the product recommendation and the relative health risk and provide to at least one of: the dental professional, the health care professional, the expert, e-commerce consumer, the individual, the e-commerce organization, the artificial intelligence system, the researcher, the manufacturer, the business, the application software, the patient portal, the system software, the client device, the insurance company, the bioinformatics organization, and the processing device over a communication network;
    wherein the communication network includes at least one of: the internet, an intranet, an extranet, an internet transaction service, an online transaction service, a mobile network, a cell phone, a wearable technology, a wireless network, a cloud platform, an online transaction processing (OLTP) service, an online analytical processing (OLAP) service, and a transaction platform and provide to at least one of: the dental professional, the health care professional, the expert, the individual, the e-commerce organization, the artificial intelligence system, the researcher, the manufacturer, the business, the application software, the system software, the client device, and the processing device.

2. A method of identifying a relative genomic health risk from at least one of: a dental image, a dental image landmark, an image, and an image landmark when matched and identified to at least one of: a deoxyribonucleic acid (DNA) sequence, a ribonucleic acid (RNA), and a genomic sequence, the method implemented by a processor, wherein the method implemented by the processor is configured to: receive at least one of: the dental image, the dental image landmark, the image, and the image landmark; wherein the method may be configured to execute an instruction in any order;
    calculate a quantitative score by weighting the level of at least one of: a deoxyribonucleic acid (DNA) sequence, an individual deoxyribonucleic acid (DNA) sequence, a ribonucleic acid (RNA) sequence, an individual ribonucleic acid (RNA) sequence, a genetic sequence, and a dataset or an expression product thereof and at least one of: the dental image, the dental image landmark, the image, and the image landmark to determine the relative genomic health risk and provide to a dental image dataset;
    determine an image variant in at least one of: the dental image, the dental image landmark, the image, and the image landmark and match it with at least one of: the deoxyribonucleic acid (DNA) sequence, the ribonucleic acid (RNA) sequence, and the genomic sequence to determine the relative genomic health risk and provide to the dental image dataset;
    determine if no image variant is detected in at least one of: the dental image, the dental image landmark, the image, and the image landmark and match it with at least one of: the deoxyribonucleic acid (DNA), sequence, the ribonucleic acid (RNA) sequence, and the genomic sequence to determine a relative genomic health risk and provide to the dental image dataset;
    match and identify the dental image dataset to the individual information dataset to generate the relative health risk and provide to the dataset;
    process a transaction of at least one of: an exchange, a transfer, a purchase, a sell of at least one of: the dental image dataset, the individual information dataset, the relative genomic health risk, and the correlation dataset over a communication network; wherein the communication network includes at least one of:
    the internet, an intranet, an extranet, an internet transaction service, an online transaction service, a mobile network, a cell phone, a wearable technology, a wireless network, a cloud platform, an online transaction processing (OLTP) service, an online analytical processing (OLAP) service, and a transaction platform.

3. A method implemented by a microprocessor for identifying a genetic probability from matching and identifying at least one of: a dental image, a dental image landmark, an image, and an image landmark the method comprising:

execute an instruction in any order;

determine a quantitative score by weighting a level of at least one of:

a deoxyribonucleic acid (DNA) sequence, an individual deoxyribonucleic acid (DNA) sequence, a ribonucleic acid (RNA) sequence, an individual ribonucleic acid (RNA) sequence, a RNA transcript sequence of a gene, a and the genetic sequence from at least one of: the genetic sequence, the genetic sample, a tissue sample, a saliva sample, a blood sample, a sample and at least one of: the dental image, the dental image landmark, the image, and the image landmark and provide to a dental image dataset; determine a quantitative score by weighting a normalized level of the deoxyribonucleic acid (DNA) sequence, the individual deoxyribonucleic acid (DNA) sequence, the ribonucleic acid (RNA) sequence, the individual ribonucleic acid (RNA) sequence, the RNA transcript sequence of the gene, and a genetic sequence of a gene to at least one reference gene and at least one of: the dental image, the dental image landmark, the image, and the image landmark to produce a normalized gene expression level and provide to the dental image dataset;

comparing the normalized gene expression level of a gene to a range of normalized gene expression levels of the reference gene obtained from at least one of: a dental anatomy reference dataset, a dental pathology reference dataset, and a reference dataset set and at least one of: associate, correlate it to at least one of: the dental image, the dental image landmark, the image, and the image landmark and provide to the dental image dataset;

predict the relative health risk of at least one of: a pathology, a dental pathology, and no pathology based on the comparison of the normalized level of at least one of: the deoxyribonucleic acid (DNA) sequence, the individual deoxyribonucleic acid (DNA) sequence, the ribonucleic acid (RNA) sequence, the individual ribonucleic acid (RNA) sequence, the RNA transcript sequence of the gene, and the genetic sequence expression level of the gene to the normalized reference gene dataset and at least one of: associate, correlate it to at least one of: the dental image, the dental image landmark, the image, the image landmark and provide to the dental image dataset;

match and identify the dental image dataset to an individual information dataset to produce at least one of: a genetic probability, the relative health risk and provide to a correlation dataset;

process a transaction of at least one of: an exchange, a transfer, a purchase, a sell of at least one of: the genetic probability, the relative health risk, and the correlation dataset over a network.

4. The method of claim 1, claim 2, or claim 3, wherein at least one of: the dental image, the dental image landmark, the image, and the image landmark is obtained from at least one of: a digital x-ray, a digital image, a cell phone captured image, a photographic image, a toothbrush with an imaging device, a toothbrush with an imaging device being a camera, a film based x-ray, a digitally scanned x-ray, a digitally captured x-ray, an intraoral scanner, a scintillator technology based image, a trans-illumination image, a fluorescence technology based image, a blue fluorescence technology based image, a laser based technology based image, a magnetic resonance image (MRI), a computed tomography (CT) scan based image, a cone beam computed tomography (CBCT) image, an image capture device, an x-ray equipment, a digital camera, a cell phone camera, an intraoral scanner, a scintillator counter, an indirect or direct flat panel detector (FPD), a charged couple device (CCD), a phosphor plate radiography device, a picture archiving and communication system (PACS), a photo-stimulable phosphor (PSP) device, and a wireless complementary metal-oxide-semiconductor (CMOS) device.

5. The method of claim 1, claim 2, or claim 3, wherein the processing device is further configured to use at least one of: a machine learning, a deep learning of at least one of: an electronic sensor measurement, a biometric sensor measurement, and a sensor to at least one of: correlate, associate to an individual information dataset to at least one of: choose, select at least one of: a dental treatment recommendation, a dental treatment recommendation for no treatment, a dental product recommendation, a dental product recommendation for no product, and a relative health risk based on at least one of: the dental image, the dental image landmark, the image, the image landmark.

6. The method of claim 1, claim 2, or claim 3; wherein at least one of: the dental image, the dental image landmark, the image, and the image landmark, the dataset is configured to compensate for at least one of: a distorted information, a missing image information.

7. The method of claim 1, claim 2, or claim 3, wherein at least one of: the dental image, the dental image landmark, the image, the image landmark is processed with at least one deep neural network layer.

8. The method of claim 1, wherein at least one of: the dental professional, the health care professional is at least one of: a dentist, a hygienist, a dental assistant, a dental staff member, a medical staff member, a dental laboratory technician, a physician, a nurse, a medical technician, a veterinarian, a veterinarian professional, and a licensed professional;

wherein the expert is at least one of: a dentist, a hygienist, a dental assistant, a dental staff member, a dental laboratory technician, a physician, a nurse, a medical staff member, and a medical technician;

wherein the e-commerce consumer is at least one of: an individual, a guardian, and an employee;

wherein the e-commerce organization is at least one of: a business, a business entity, a business owner, an employer, a wholesaler, a retailer, a group, a research entity, a law enforcement entity, a public administration entity, a government agency, an administrator, an administrator entity, a governing agency, a bioinformatics service, an insurance company, and a cloud based storage service;

wherein the artificial intelligence system is at least one of: an artificial intelligence system, an artificial intelligence model, and an artificial intelligence dataset;

wherein a researcher is at least one of: a teacher, a professor, an educator, an academic professional, a scientist, and a statistician;

wherein the client device is at least one of: a server, a desktop computer, a workstation, a laptop computer, a cell phone, a tablet, a mobile device, and a cloud based storage service.

9. The method of claim 1, claim 2, or claim 3 wherein the method implements by at least one of a processor, a microprocessor is configured to provide at least one of: a real time treatment recommendation, a real time dental treatment recommendation a real time dental product recommendation, a real time dental product recommendation, a real time relative health risk, a real time genetic probability, and a real time relative genomic health risk.

10. A method of predicting at least one of: a product recommendation, a treatment recommendation, a likelihood of a clinical genomic outcome of an individual from at least one of: a dental image, a dental image landmark, an image, and an image landmark based on matching and identifying to at least one of: a deoxyribonudeic acid (DNA) sequence, an ribonucleic acid (RNA) sequence, a ribonucleic acid (RNA) transcripts sequence, a genetic sequence, and an expression product in a biological sample; the method comprising: a computer vision component configured to analyze at least one of: the dental image, the dental image landmark, the image, and the image landmark; implementing the method by a memory configured to store instructions associated with an aggregator and implementing by a processor coupled to the computer vision component and the memory, the method implemented by the processor executing instructions associated with the aggregator, wherein the method includes:
an image processing engine configured to receive at least one of: the dental image, the dental image landmark, the image, and the image landmark
the method may execute an instruction in any order;
match and identify a level at least one of: the deoxyribonucleic acid (DNA) sequence, the ribonucleic acid (RNA) sequence, the ribonucleic acid (RNA) transcripts sequence, the genetic sequence, and the expression product in the biological sample to at least one of: the dental image, the dental image landmark, the image, and the image landmark and provide to a bioinformatics dataset;
match and identify at least one of: the deoxyribonucleic acid (DNA) sequence, the ribonucleic acid (RNA) sequence, the ribonucleic acid (RNA) transcripts sequence, the genetic sequence, and the expression product in the biological sample to one or more gene groups selected from at least one of: a cellular organization gene group, a basal epithelia gene group, a stress response gene group, an androgen gene group, a stromal response gene group, a proliferation gene group, a dataset to at least one of: the dental image, the dental image landmark, the image, and the image landmark and provide to a bioinformatics dataset;
calculating quantitative score for the individual by weighting level of at least one of:
the deoxyribonucleic acid (DNA) sequence, the ribonucleic acid (RNA) sequence, the ribonucleic acid (RNA) transcripts sequence, the genetic sequence, and expression product in a biological sample obtained from the individual to at least one of: the dental image, the dental image landmark, the image, and the image landmark and provide to the bioinformatics dataset;
correlate at least one of: the dental image, the dental image landmark, the image, and the image landmark of the individual with at least one of: the deoxyribonucleic acid (DNA) sequence, the ribonucleic acid (RNA) sequence, the ribonucleic acid (RNA) transcripts sequence, the genetic sequence, and the expression product in the biological sample obtained from the individual and provide to the bioinformatics dataset;
predicting likelihood of clinical genomic outcome of the individual based on a quantitative score from at least one of: the dental image, the dental image landmark, the image, and the image landmark of the individual with at least one of: the deoxyribonucleic acid (DNA) sequence, the ribonucleic acid (RNA) sequence, the ribonucleic acid (RNA) transcripts sequence, the genetic sequence, and the expression product in the biological sample obtained from the individual and provide to the bioinformatics dataset;
process a transaction of at least one of: an exchange, a transfer, a buy, a sell with at least one of: the dental image, the dental image landmark, the image, the image landmark, the dental treatment recommendation, the dental product recommendation, the likelihood of a clinical genomic outcome of the individual, and the bioinformatics dataset, over a communication network, wherein the communication network includes at least one of: the internet, an intranet, an extranet, an internet transaction service, an online transaction service, a mobile network, a cell phone, a wearable technology, a wireless network, a cloud platform, an online transaction processing (OLTP) service, an online analytical processing (OLAP) service, a transaction platform and provide to at least one of: a dental professional, a health care professional, an expert, the individual, an e-commerce organization, a researcher, a manufacturer, a business, an application software, a system software, a client device an artificial intelligence system, and processing device.

11. The method of claim 10, wherein at least one of: the dental professional, the health care professional is at least one of: a dentist, a hygienist, a dental assistant, a dental staff member, a medical staff member a dental laboratory technician, a physician, a nurse, a medical technician, a veterinarian, a veterinarian professional, and a licensed professional;
wherein the expert is at least one of: the dentist, the hygienist, the dental assistant, the dental staff member, the dental laboratory technician, the physician, the nurse, a medical staff member, and a medical technician;
wherein the individual is at least one of: a guardian, and an employee;
wherein the e-commerce organization is at least one of: the business, a business entity, a business owner, an employer, a wholesaler, a retailer, a group, a research entity, a law enforcement entity, a public administration entity, a government agency, an administrator, an administrator entity, a governing agency, a bioinformatics service, an insurance company, and a cloud based storage service;
wherein the artificial intelligence system is at least one of: an artificial intelligence model, an artificial intelligence dataset;
wherein the researcher is at least one of: a teacher, a professor, an educator, an academic professional, a scientist, and a statistician.

12. The method of claim 10, wherein the method further comprises performing the steps of:

verify a compliance of the individual with a regulatory policy;

verify an authorization by the individual to analyze at least one of: the dental image, the dental image landmark, the image, and the image landmark;

authenticate the individual to process a transaction of at least one of: an exchange, a transfer, a buy, a sell of at least one of:

the dental image, the dental image landmark, the image, the image landmark, the dental treatment recommendation, a dental product recommendation, and the likelihood of a clinical genomic outcome of the individual.

13. The method of claim 10, where the artificial intelligence system may be configured to select at least one of: the dental treatment recommendation, a dental treatment recommendation for no treatment, the dental product recommendation, a dental product recommendation for no product, and the likelihood of a clinical genomic outcome of the individual based on at least one of: the dental image, the dental image landmark, the image, and the image landmark based on matching and identifying to at least one of: the deoxyribonucleic acid (DNA) sequence, the ribonucleic acid (RNA) sequence, the ribonucleic acid (RNA) transcripts sequence, the genetic sequence, and the expression product in the biological sample.

14. The method of claim 10, wherein the individual includes a dataset of at least one of: an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, an internet protocol address, a change of insurance, an employer, a change of employment, a change of zip code, a change of previous medication, a change of a marital status, a change of gender, a location, a change of location, a biometric measurement, a biometric sensor measurement, a genetic sequence, an individual deoxyribonucleic acid (DNA) sequence, an individual ribonucleic acid (RNA) sequence, an internet browsing history, and a dataset.

15. The method of claim 10, further configured to correlating at least one of: the dental image, the dental image landmark, the image, and the image landmark with a genetic sequence to generate a genetic connection;

where in the genetic sequence includes at least one of: a node, a genotype, a gene identifier, a gene sequence, a single nucleotide polymorphism, a nucleic acid sequence, a protein sequence, an annotating genome, a shotgun sequence, a periodontal disease, a caries susceptibility, a malocclusion, a pathology, an impacted tooth, a tooth loss, an angle's classification of malocclusion, a diabetes diagnosis, and a medical condition;

determining a weight associated with genetic connection between two directly connected nodes;

determine the shortest genetic connection path;

determining a weight associated with each genetic connection between two directly connected nodes;

and provide to the bioinformatics dataset.

16. The method of claim 10, wherein the the bioinformatics dataset includes a bioinformatics service, and wherein the bioinformatics service provides a dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, and a diabetes diagnosis;

wherein, the bioinformatics dataset may be correlated to an individual information dataset.

17. The method of claim 10, is further configured to generate, using the processor, a notification based on an analyzing.

18. The method of claim 10, is further configured to with at least one of: the dental treatment recommendation, the treatment recommendation, the dental product recommendation, the product recommendation, and the relative health risk.

19. The method of claim 10, wherein the method is further configured for merging at least one of:

the product recommendation, the treatment recommendation, and the likelihood of a clinical genomic outcome of an individual to an artificial intelligence dataset, wherein an analyzing of at least one of: the product recommendation, the treatment recommendation, and the likelihood of a clinical genomic outcome of an individual may be based on the artificial intelligence dataset.

20. The method of claim 10, wherein the processing of at least one of: the dental image, the dental image landmark, the image, and the image landmark based on matching and identifying to at least one of: the deoxyribonucleic acid (DNA) sequence, the ribonucleic acid (RNA) sequence, the ribonucleic acid (RNA) transcripts sequence, the genetic sequence, and the expression product in a biological sample is based on at least one artificial intelligence model, wherein at least one artificial intelligence model is configured for determining of at least one of:

the treatment recommendation, the product recommendation, and the likelihood of a clinical genomic outcome of an individual.

* * * * *